US006234996B1

(12) United States Patent
Bagaoisan et al.

(10) Patent No.: US 6,234,996 B1
(45) Date of Patent: May 22, 2001

(54) INTEGRATED INFLATION/DEFLATION DEVICE AND METHOD

(75) Inventors: Celso J. Bagaoisan, Union City; George Tsai, Sunnyvale; Samuel L. Omaleki, Morgan Hill; Roy Leguidleguid, Union City; Gholam-Reza Zadno-Azizi, Newark, all of CA (US)

(73) Assignee: PercuSurge, Inc., Sunnyvale, CA (US)

( * ) Notice: Subject to any disclaimer, the term of this patent is extended or adjusted under 35 U.S.C. 154(b) by 0 days.

(21) Appl. No.: 09/338,375

(22) Filed: Jun. 23, 1999

(51) Int. Cl.[7] ................................................. A61M 29/00
(52) U.S. Cl. ................................... 604/97.01; 604/97.03; 604/99.01
(58) Field of Search ........................... 604/97.01, 97.02, 604/97.03, 98.01, 99.01, 99.02, 99.03, 100.01, 100.02, 100.03, 96.01

(56) References Cited

U.S. PATENT DOCUMENTS

| | | |
|---|---|---|
| 3,401,692 | 9/1968 | Harris, Jr. . |
| 4,023,716 | 5/1977 | Shapiro . |
| 4,024,865 | 5/1977 | Howlett . |
| 4,205,683 | 6/1980 | O'Neill . |
| 4,332,254 | 6/1982 | Lundquist . |
| 4,471,765 | 9/1984 | Strauss et al. . |
| 4,581,015 | 4/1986 | Alfano . |
| 4,592,746 | 6/1986 | Burkholder et al. . |
| 4,713,060 | 12/1987 | Riuli . |
| 4,740,203 | 4/1988 | Hoskins et al. . |
| 4,758,223 | 7/1988 | Rydell . |
| 4,803,999 | 2/1989 | Liegner . |
| 5,090,962 | 2/1992 | Landry, Jr. et al. . |
| 5,167,239 | 12/1992 | Cohen et al. . |
| 5,196,017 | 3/1993 | Silva et al. . |
| 5,209,732 | 5/1993 | Lampropoulos et al. . |
| 5,250,030 | 10/1993 | Corsich . |
| 5,304,147 | 4/1994 | Johnson et al. . |
| 5,308,341 | 5/1994 | Chanoch . |
| 5,370,620 | 12/1994 | Shonfeld . |
| 5,472,424 | 12/1995 | Lampropoulos et al. . |
| 5,531,721 | 7/1996 | Pepin et al. . |
| 5,607,399 | 3/1997 | Grimard et al. . |
| 5,647,847 | 7/1997 | Lafontaine et al. . |
| 5,647,856 | 7/1997 | Eykmann et al. . |

FOREIGN PATENT DOCUMENTS

| | | |
|---|---|---|
| 0 446 932 A2 | 9/1991 | (EP) . |
| 0511 402 A1 | 11/1992 | (EP) . |
| 0547 358 A2 | 6/1993 | (EP) . |
| 0 799 993 A2 | 10/1997 | (EP) . |
| WO 89/09071 | 10/1989 | (WO) . |
| WO 95/33510 | 12/1995 | (WO) . |
| WO 98/11926 | 3/1998 | (WO) . |
| WO 98/56440 | 12/1998 | (WO) . |

Primary Examiner—John D. Yasko
(74) Attorney, Agent, or Firm—Knobbe, Martens, Olson & Bear, LLP.

(57) ABSTRACT

An integrated inflation/deflation device provides easy, precise delivery of a small amount of fluid for proper inflation of a low volume surgical balloon and similarly provides easy and fast deflation of the balloon. A preferred embodiment includes a low volume syringe and large syringe mounted together within a housing. A port in the low volume syringe is in communication with the large syringe barrel. The low volume syringe plunger is controlled by a knob disposed on the housing. The large syringe is used to prime the surgical balloon system, including a catheter, and the low volume syringe delivers a precise, predetermined volume of fluid to inflate the balloon. The low volume syringe is also used to deflate the balloon. Preferably, indicia on the housing adjacent the knob direct the required rotation of the knob to deliver the correct volume of fluid to be injected to match a balloon of a given size and shape so that the balloon is properly inflated.

25 Claims, 35 Drawing Sheets

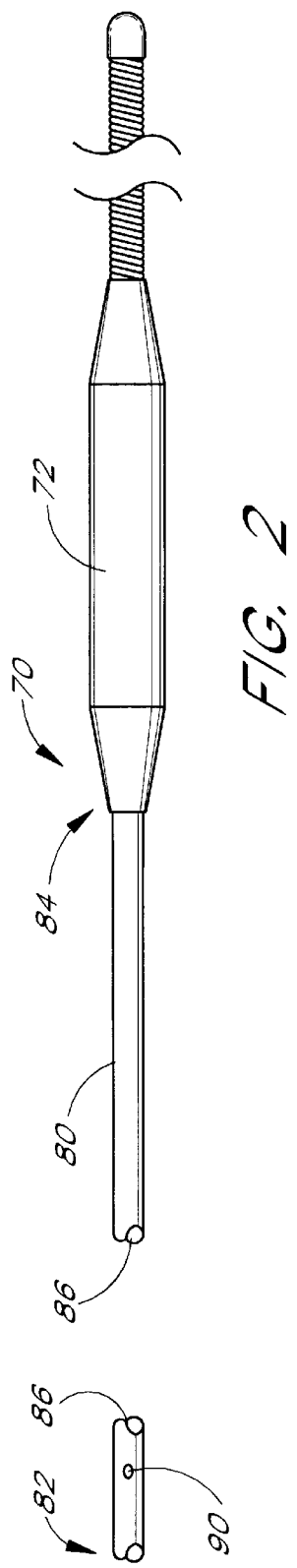

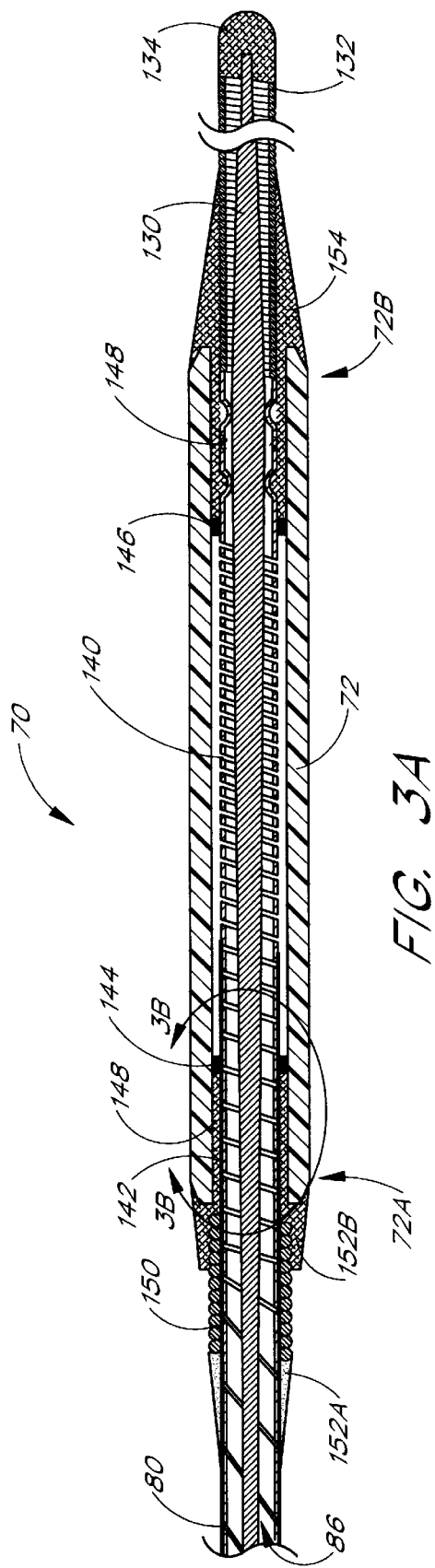
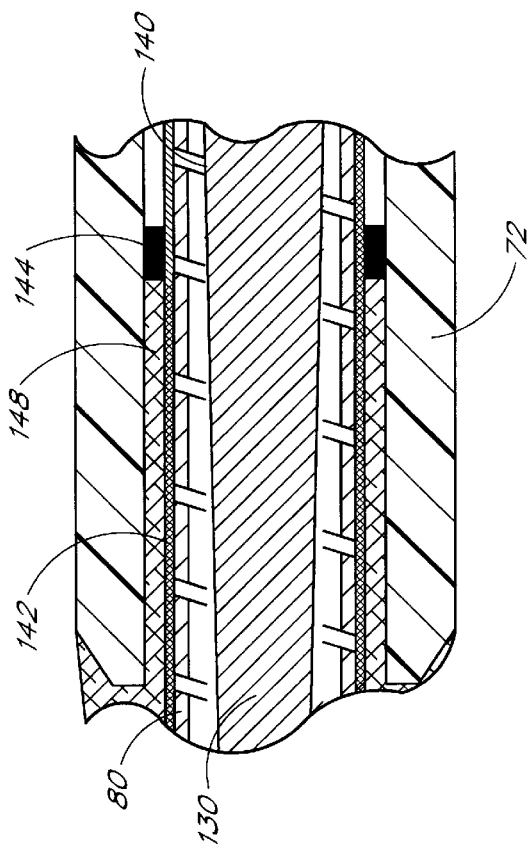
FIG. 3A
FIG. 3B

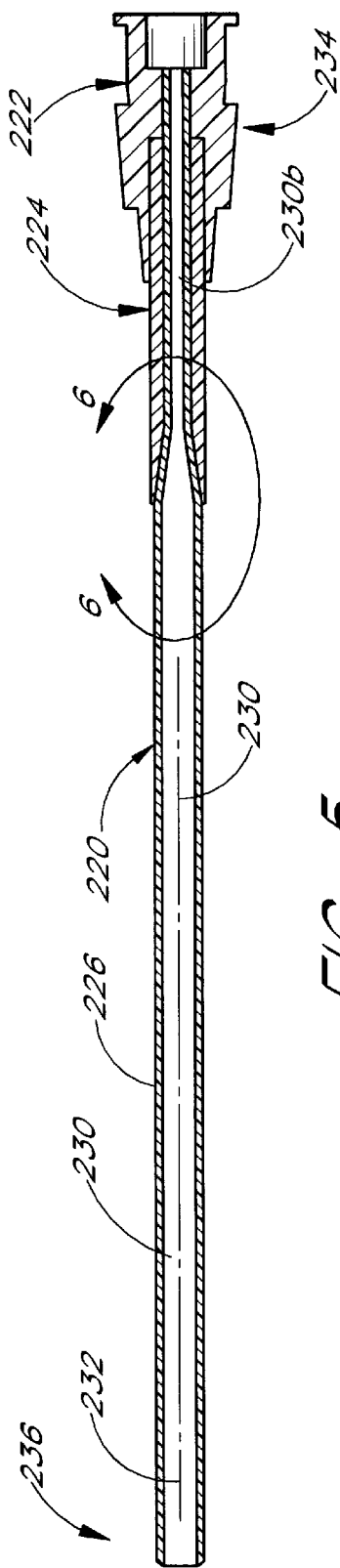
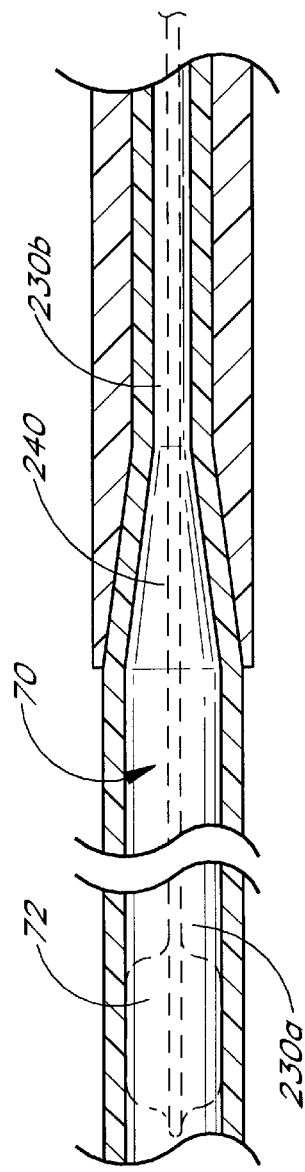
FIG. 5
FIG. 6

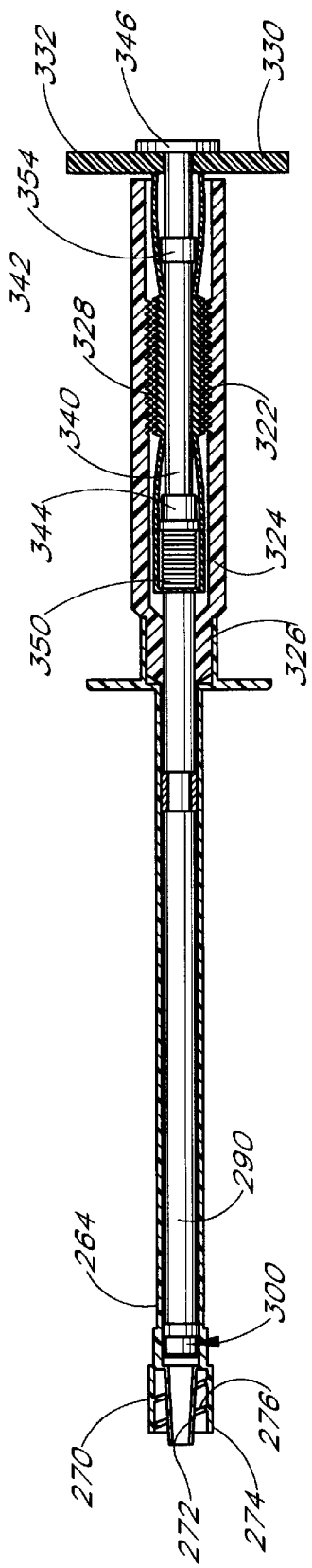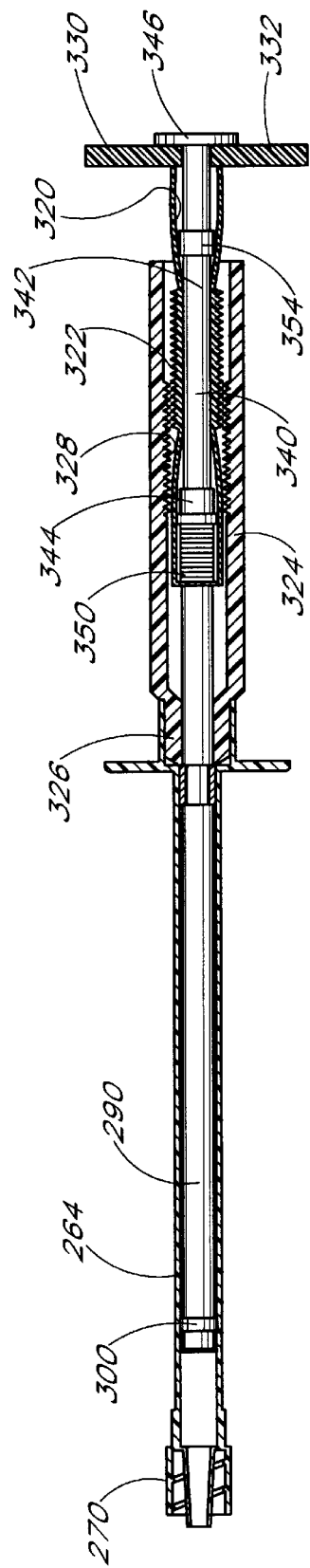

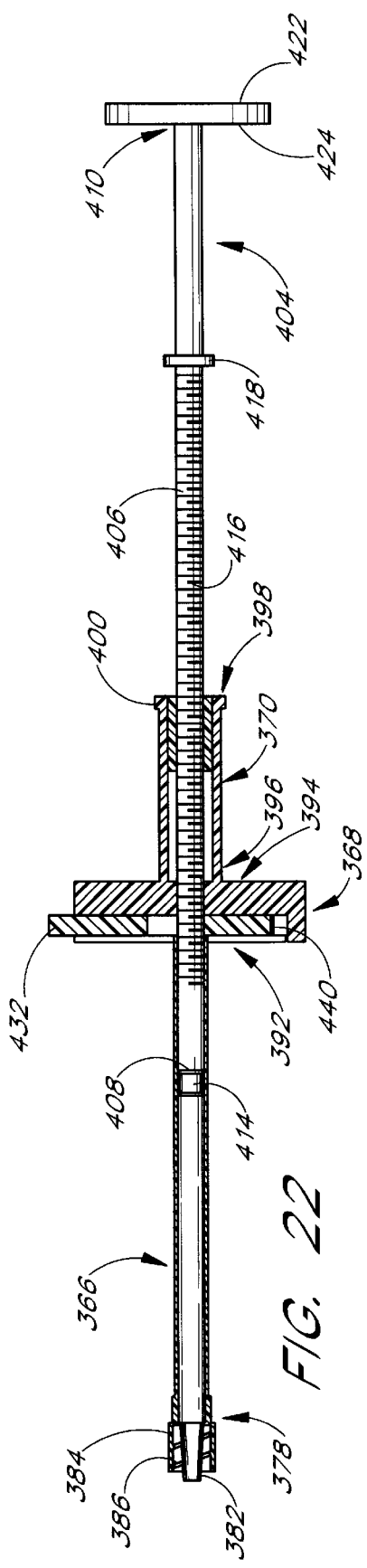
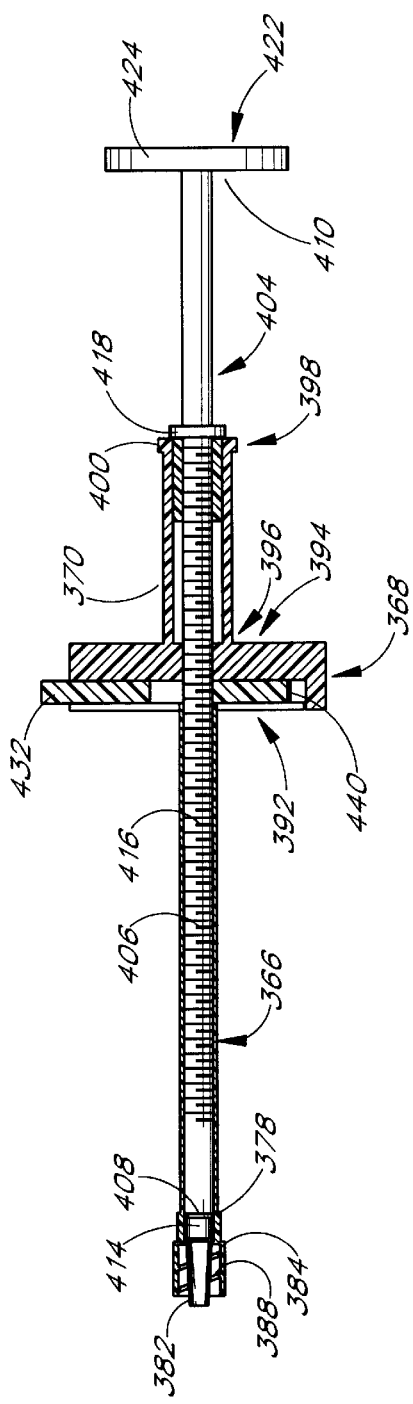

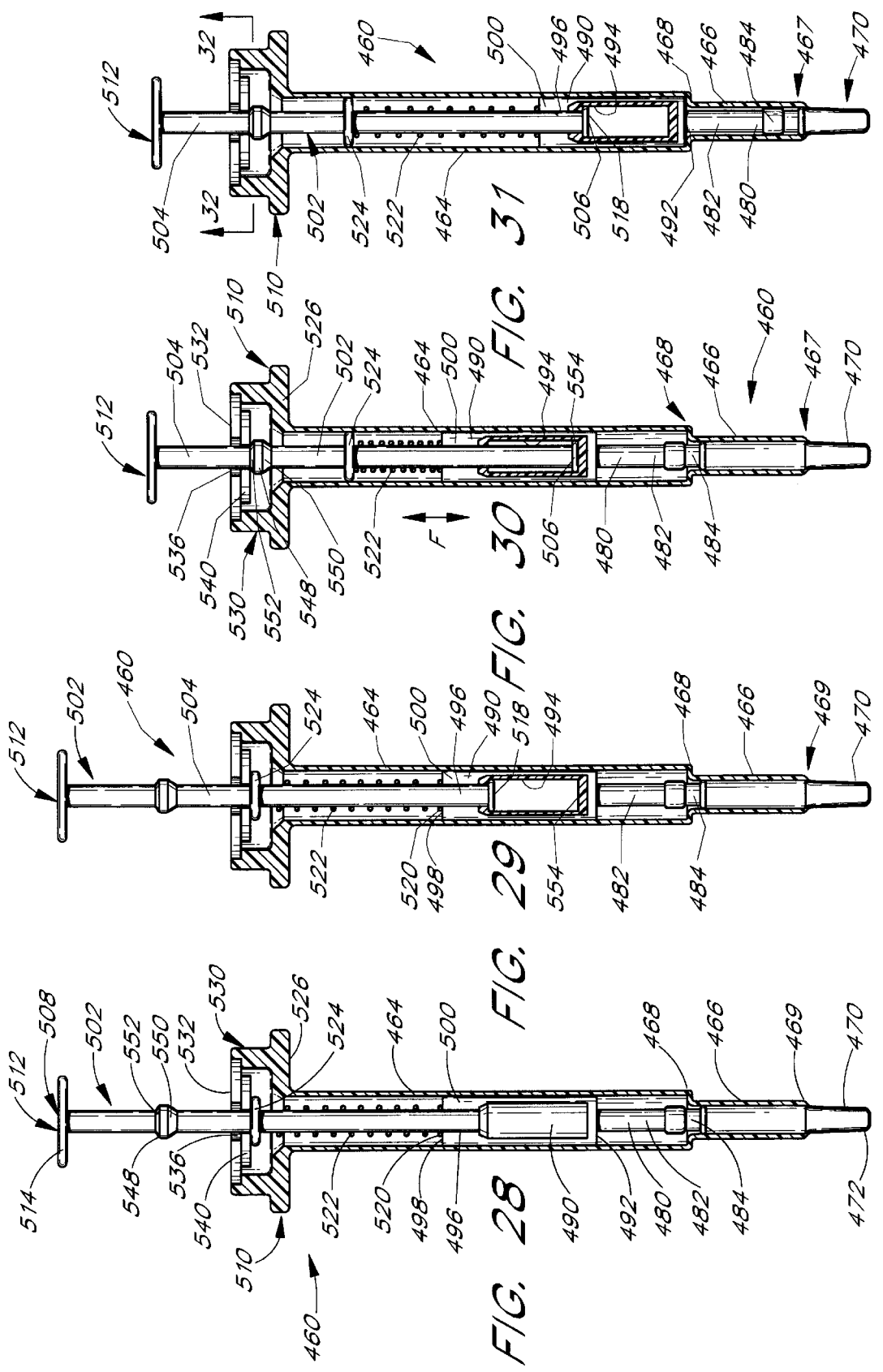

INTEGRATED INFLATION/DEFLATION DEVICE AND METHOD

BACKGROUND OF THE INVENTION

1. Field of the Invention

The present invention relates generally to an apparatus and method of properly inflating and deflating a surgical balloon and, in particular, to an integrated balloon inflation/deflation device and a method of using the same in a convenient and precise manner without damaging healthy tissue.

2. Description of the Related Art

Surgical balloons are used for procedures such as percutaneous transluminal angioplasty for treatment of stenosis and for occluding blood vessels to prevent release of emboli into the bloodstream during such procedures. During this type of procedure, a guidewire is conventionally used to guide the insertion of the medical instrument, such as a balloon catheter, to the desired treatment site within a patient's vasculature. A hollow guidewire or guidewire catheter with a balloon at its distal tip is often used to anchor the guidewire at the treatment site. A medical instrument such as an occlusion balloon catheter for emboli containment may have multiple lumens and a pair of occlusion balloons. Alternatively, the balloon on the guidewire or catheter may be used for the occlusion of the vessel downstream of the treatment site.

Surgical balloons are typically made of compliant material and increase in diameter with increasing inflation pressure until the balloon burst pressure is reached. Surgical balloons such as occlusion balloons and balloons used for anchoring guidewires must be expanded to contact the blood vessel wall. Clinicians, however, often do not know exactly when the balloon has contacted the blood vessel walls, if uniform circumferential occlusion has been accomplished or whether the balloon has been overinflated.

Conventional surgical balloons are inflated with a syringe coupled to the proximal end of the catheter. The syringe, which is located external to the patient, typically has a fluid capacity of anywhere from 0.5 cc to 10 cc and the clinician uses the syringe to inflate the balloon. The clinician must have considerable patience, skill and concentration to accurately deliver a suitable volume of fluid, such as 0.05 cc, to properly inflate the balloon.

The clinician must also be extremely careful not to overinflate the balloon. Although a pressure gauge is provided on some syringes, the skill required to avoid overinflation is still beyond many clinicians because a very small movement of the syringe piston results in a relatively large injection of fluid. For example, if the clinician desires to deliver about 0.1 cc of fluid to the balloon from a conventional 10 cc syringe, the travel of the syringe piston is less than about 0.7 mm. Thus, it can be readily seen that the control of the syringe to this degree of precision is very difficult. Additionally, unlike therapeutic balloons (which require about 20 atmospheres pressure and can use syringes ranging between about 10 to 20 cc in fluid capacity), typical occlusion balloons require less than about 3 atmospheres pressure and require less than about 1 cc of fluid. Because occlusion balloons are inflated to relatively low pressures with small amounts of fluids, the clinician must be very careful when using a conventional syringe to inflate the balloon.

The risks of imprecision while inflating a surgical balloon with a conventional syringe are substantial. For example, overinflation of the occlusion balloon may cause it to rupture, releasing inflation media into the bloodstream (e.g., fluid, air, gas, etc.), and possibly allowing pieces of the balloon to enter the bloodstream. In addition, the balloon will fail to occlude emboli or anchor the guidewire. Overinflation of the balloon can also damage the healthy tissue adjacent the vessel segment undergoing treatment, even if the balloon does not rupture. The radial expansion of the balloon can also cause undesirable pressure on the vessel wall, and longitudinal expansion of the balloon can create a shearing force which could lead to vessel trauma. Further, if the balloon is overinflated, it may experience a decrease in fatigue strength. For example, if a surgical balloon is overinflated such that it is approximately two to three times its original working length, the balloon may experience a significant decrease in fatigue strength. Underinflation of the balloon also causes many difficulties and problems. An underinflated balloon, for example, may allow fluid to flow around the balloon and the balloon may fail to occlude emboli or anchor the guidewire in the desired position.

Thus, there is a need for a low volume syringe to provide accurate delivery of a suitable amount of fluid to a surgical balloon.

It is also very difficult for the clinician to deliver the desired volume of fluid and then maintain the syringe in a fixed location such that the volume of fluid does not subsequently change. For example, once the clinician has depressed the plunger of the syringe a desired amount to properly inflate the balloon, the clinician must hold the plunger in that position until the pressure equalizes and/or it is desired to deflate the balloon. As discussed above, even small movements of the syringe plunger may cause overinflation or underinflation of the balloon. Thus, the clinician must be very careful not to allow the plunger to move even a very small distance after the fluid is delivered because that may effect the amount of fluid delivered by the syringe.

Thus, a need exists for a syringe which delivers a desired volume of fluid and then does not allow that volume of fluid to be unintentionally changed.

In addition to the problems of overinflation, another problem exists when inflating occlusion balloons. As discussed above, even though the pressure required to inflate the occlusion balloon is generally less than 3 atmospheres, the pressure caused by a conventional inflation syringe causes an immediate build up of pressure near the syringe. The build up of pressure can reach magnitudes of 400 psi. This high pressure caused by conventional syringes often causes leaks in the system and it may damage the balloon. Additionally, this high pressure makes it very difficult for the clinician to properly inflate the balloon to the desired size and pressure.

Thus, there is a need for a syringe that does not create the high build up of pressure created by conventional syringes.

SUMMARY OF THE INVENTION

A need exists for a low volume syringe which inflates surgical balloons without the above-described problems and disadvantages.

The present invention is an apparatus and method for inflating and deflating surgical balloons and, in particular, inflating and deflating surgical balloons requiring minimal amounts of inflation fluid. Desirably, the apparatus and method includes a syringe assembly which inflates and deflates surgical balloons for proper contact with a wall in a human body, such as a vessel wall, without damage to the wall.

Preferred embodiments of the present invention are illustrated below in connection with a guidewire catheter having an occlusion balloon attached. It will be appreciated, however, that the present invention is readily adapted for use with other medical devices requiring small inflation volumes, for example, to prevent balloon rupture and/or damage to the surrounding tissue. In addition, the present invention can be used with somewhat larger balloons, such as therapeutic balloons for angioplasty procedures, where the enhanced control of the delivery of the inflation fluid is beneficial. The present invention also provides important benefits for non-angioplasty balloon procedures, as well as certain non-balloon applications where inflation/injection and/or deflation/evacuation are utilized.

In a preferred embodiment having features in accordance with the present invention, a syringe is provided for use in medical procedures requiring relatively accurate volumetric delivery of fluids at a relatively slow rate. The syringe includes an elongate hollow body comprising a barrel and a plunger guide. The plunger guide is threaded along an interior surface. A plunger is longitudinally slidable within the barrel to effect intake and outflow of the fluids. The plunger has a shaft with a collapsible chamber formed near the proximal end. Outer threads are formed on outer surfaces of the shaft around the chamber. A plunger actuator is slidably disposed at least partially within the chamber. The plunger actuator has a head sized and adapted to prevent the chamber from collapsing when the head is disposed medially between proximal and distal ends of the chamber. Thus, when the head is disposed between the ends of the chamber, the plunger shaft threads are forced into engagement with the plunger guide threads and the plunger can be advanced or retracted within the barrel by interaction of the threads.

In another embodiment having features in accordance with the present invention, a syringe is provided for use in medical procedures requiring relatively accurate volumetric delivery of fluids at a relatively slow rate. The syringe has a hollow elongate body with a distal end and a proximal end. A portion of an inner surface of the body is threaded. A plunger is provided having a hollow chamber extending longitudinally between at least two plunger shaft walls. Outer surfaces of the shaft walls are threaded. The syringe further includes an actuator having a support member slidably disposed within the chamber. The support member is sized and adapted to support the shaft walls and urge the shaft threads into engagement with the body threads.

In yet another embodiment having features in accordance with the present invention, a syringe adapted for use in medical procedures requiring accurate volumetric delivery of fluids at a relatively slow rate is provided having an elongate hollow body. A plunger is longitudinally slidable within the body to effect intake and outflow of the fluids and has a partially threaded shaft. A housing is positioned between distal and proximal ends of the body and a threading member is slidably disposed in the housing to selectively engage the shaft threads. The threading member is preferably spring biased toward engaging the shaft threads. When the threading member is engaged with the shaft threads, an accurate delivery of fluid by the syringe at a slow, controlled rate is achieved by rotating the plunger. When the threading member is released from engaging the shaft threads, the plunger may be slid uninhibited by threads within the body.

In another embodiment having features in accordance with the present invention, a syringe adapted for use in medical procedures requiring relatively accurate volumetric delivery of fluids at a regulated pressure is provided. The syringe has a hollow elongated body having proximal and distal ends and a plunger longitudinally slidable within the body. A piston is provided at a distal end of the plunger and a shuttle is attached to a proximal end of the plunger. The syringe further includes an actuator longitudinally movable within the body. The actuator has a shaft with a ridge formed thereon and has a proximal end extending from the proximal end of the body. A spring is disposed between the shuttle and the actuator ridge. When the actuator is depressed, the spring is compressed and exerts a spring force which advances the shuttle toward the distal end of the body, thus correspondingly advancing the plunger within the barrel. Preferably, the spring has a spring constant selected to prevent overpressurization of the fluid being delivered by the syringe.

In a still further embodiment having features in accordance with the present invention, a syringe assembly is provided. The syringe assembly is adapted for use with a low volume surgical balloon attached to an elongated tube having a sealed distal end and an inflation lumen for a communicating fluid to the balloon. The assembly includes a low volume syringe with an elongated body with proximal and distal ends. A connector is provided on the distal end and a port is formed through the body between the proximal and distal ends. A plunger is longitudinally slidable within the body and has a shaft with a piston disposed on a shaft distal end. A gear rack extends proximally from a shaft proximal end. A large volume syringe is also provided and has a relatively large fluid capacity. The large volume syringe comprises an elongated hollow body with proximal and distal ends. A plunger is longitudinally slidable within the body and has a shaft with a piston disposed on a distal end and a handle on a proximal end. The syringe body distal end has an opening in communication with a channel leading to the low volume syringe port. The syringe assembly also includes a housing adapted to substantially enclose both the low volume syringe and the large volume syringe. The housing includes a knob in communication with a gear which is adapted to engage the gear rack.

In another embodiment having features in accordance with the present invention, a method of using the above syringe assembly is provided. The method includes the steps of positioning the knob at a deflation position at which the low volume syringe piston is disposed adjacent a proximal edge of the port. A source of inflation fluid for the balloon is provided and the distal connector is attached to the source of inflation fluid. The large volume syringe handle is pulled to fill the syringe with a predetermined volume of inflation fluid. The distal connector is detached from the source of inflation fluid and attached to the elongated tube so that the syringe is in communication with a tube lumen. The knob is next rotated to a predetermined position. Thus, the syringe assembly delivers a predetermined amount of fluid as defined by the predetermined position.

In a still further embodiment having features in accordance with the present invention, a syringe assembly is provided for use in medical procedures requiring relatively accurate volumetric delivery of fluids. The syringe assembly includes an inflation syringe with an inflation lumen having proximal and distal ends. A connector is disposed at the distal end and a port is formed through the side of the inflation lumen between the proximal and distal ends. A first plunger having proximal and distal ends is longitudinally slidable within the inflation lumen to effect fluid intake and outflow. A reservoir syringe has a reservoir lumen with proximal and distal ends, the distal end in communication with the inflation port. A second plunger is provided and is longitudinally slidable within the reservoir lumen.

In yet another embodiment having features in accordance with the present invention, a method of easily and precisely inflating a balloon catheter comprising an elongated tube with a surgical balloon attached thereto is provided. The tube has a longitudinally extending lumen communicating with the balloon for inflation thereof. The method includes inserting and positioning the tube and balloon at a desired position within a blood vessel of a patient. A syringe assembly is provided comprising an inflation syringe having an inflation lumen and a reservoir syringe having a reservoir lumen. A port is provided through a side of the inflation lumen and channel is provided connecting a distal end of the reservoir lumen to the inflation lumen port. An inflation plunger is provided within the inflation lumen and a reservoir plunger is provided within the reservoir lumen. The inflation plunger is positioned so that a distal end of the inflation plunger is immediately adjacent a proximal side of the port. The proximal portion of the tube is connected to a distal end of the inflation lumen. The reservoir plunger is pulled to effect evacuation of air or fluid within the tube and the balloon into the reservoir lumen. The inflation plunger is pushed to deliver the predetermined amount of fluid to the tube and balloon. Thus, the fluid inflates the balloon to an appropriate size without rupture of the balloon or damage to the blood vessel of the patient.

Further aspects, features and advantages of the present invention will become apparent to those skilled in the art from the following detailed description of the preferred embodiments and the drawings referenced herein, the invention not being limited to any particular embodiment.

BRIEF DESCRIPTION OF THE DRAWINGS

FIG. 2 is a side view of a balloon catheter of the present invention.

FIG. 3A is a longitudinal cross-sectional view of a balloon catheter incorporating a multiple tapered core wire.

FIG. 3B is an enlarged view of the proximal end of the balloon of FIG. 3A.

FIG. 5 is a side cross-sectional view of the protective sheath assembly of FIG. 4;

FIG. 6 is an enlargement of the transition section of the protective sheath assembly of FIG. 5 as indicated by line 6—6;

FIGS. 15–18 are cross-sectional views showing the syringe of FIG. 14 in various stages of operation;

FIGS. 22 and 23 are cross-sectional views of the syringe of FIG. 21, showing a syringe plunger engaged with a lock tab;

FIG. 28 is a cross-sectional view of another embodiment of an integrated inflation/deflation syringe having features in accordance with the present invention;

FIGS. 29–31 are cross-sectional views showing the syringe of FIG. 28 in various operational stages;

DETAILED DESCRIPTION OF THE PREFERRED EMBODIMENT

The present invention involves a low volume syringe assembly and a method for inflating and deflating surgical balloons. The principles of the present invention, however, are not limited to inflating surgical balloons. It will be understood that, in light of the present disclosure, the syringe assembly can be successfully used to control the movement of fluids such as irrigation fluid, blood or therapeutic drugs.

I. Overview of Occlusion System

A. Syringe Assembly

Figure 1:
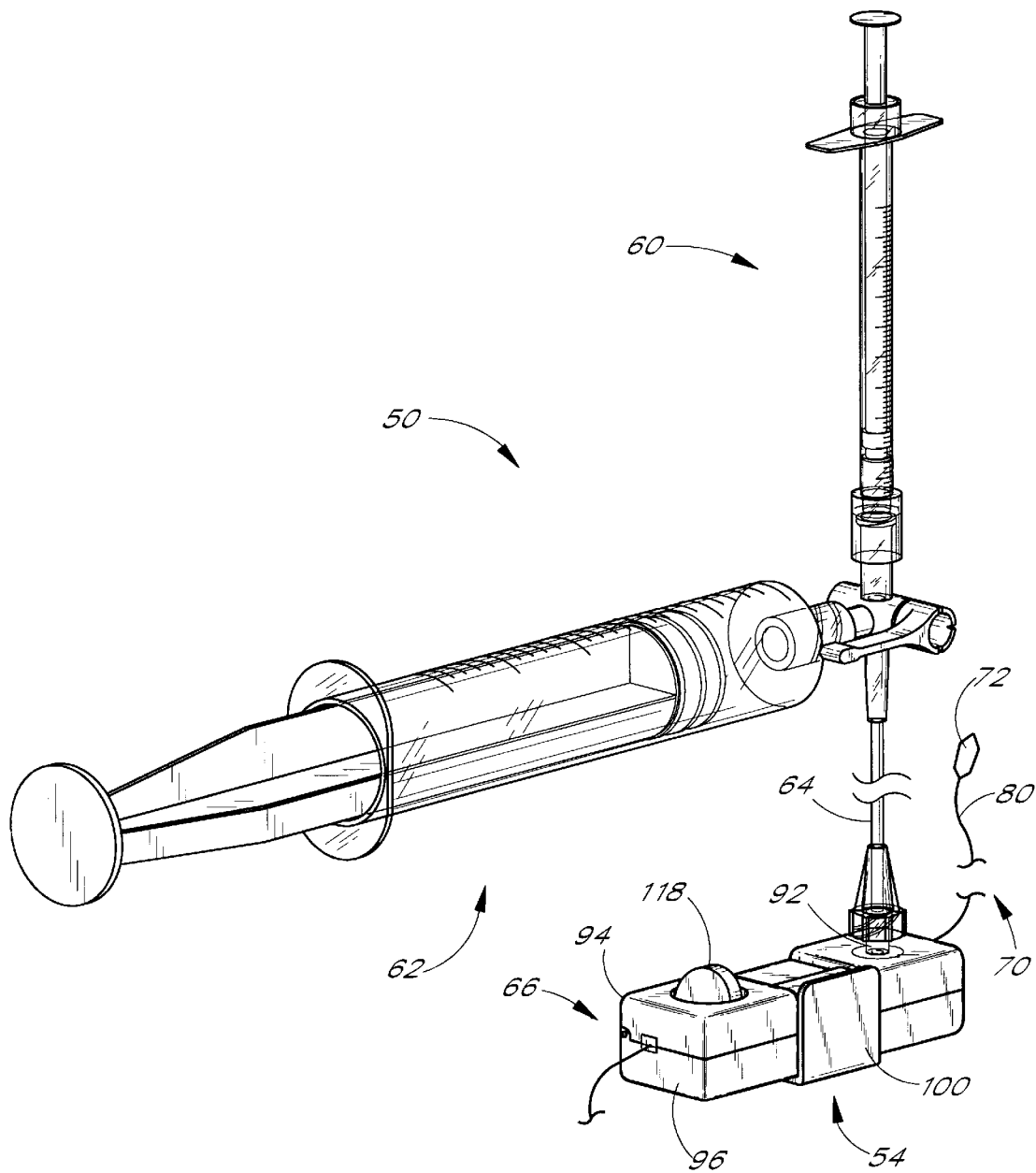
FIG. 1 shows an embodiment of a syringe assembly having features in accordance with the present invention and operably coupled to an illustrative inflation adapter at a proximal portion of a balloon catheter.

The preferred embodiments of the present invention may comprise or be used in conjunction with a syringe assembly such as that generally illustrated in FIG. 1. Also shown in FIG. 1 is an illustrative connection of the syringe assembly 50 to an occlusion balloon guidewire catheter 70 utilizing an inflation adapter 54. The syringe assembly 50, comprising the inflation syringe 60 and a larger capacity or reservoir syringe 62, is attached via tubing 64 to the inflation adapter 54 within which a low profile catheter valve 66 and the balloon catheter 70 are engaged during use.

Figure 7:
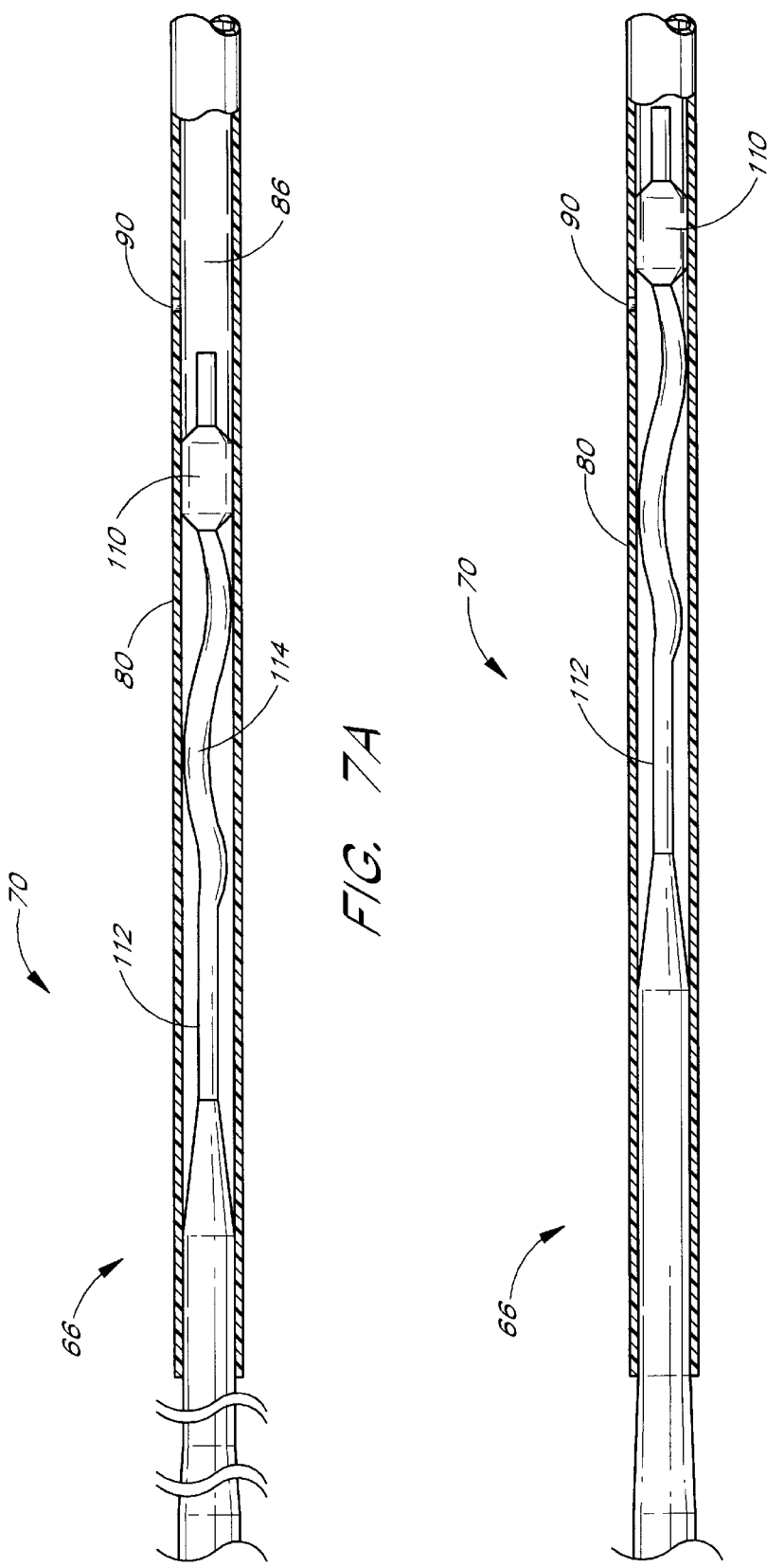
FIGS. 7A and 7B show the open and closed low profile catheter valve positions, respectively.
Figure 8:
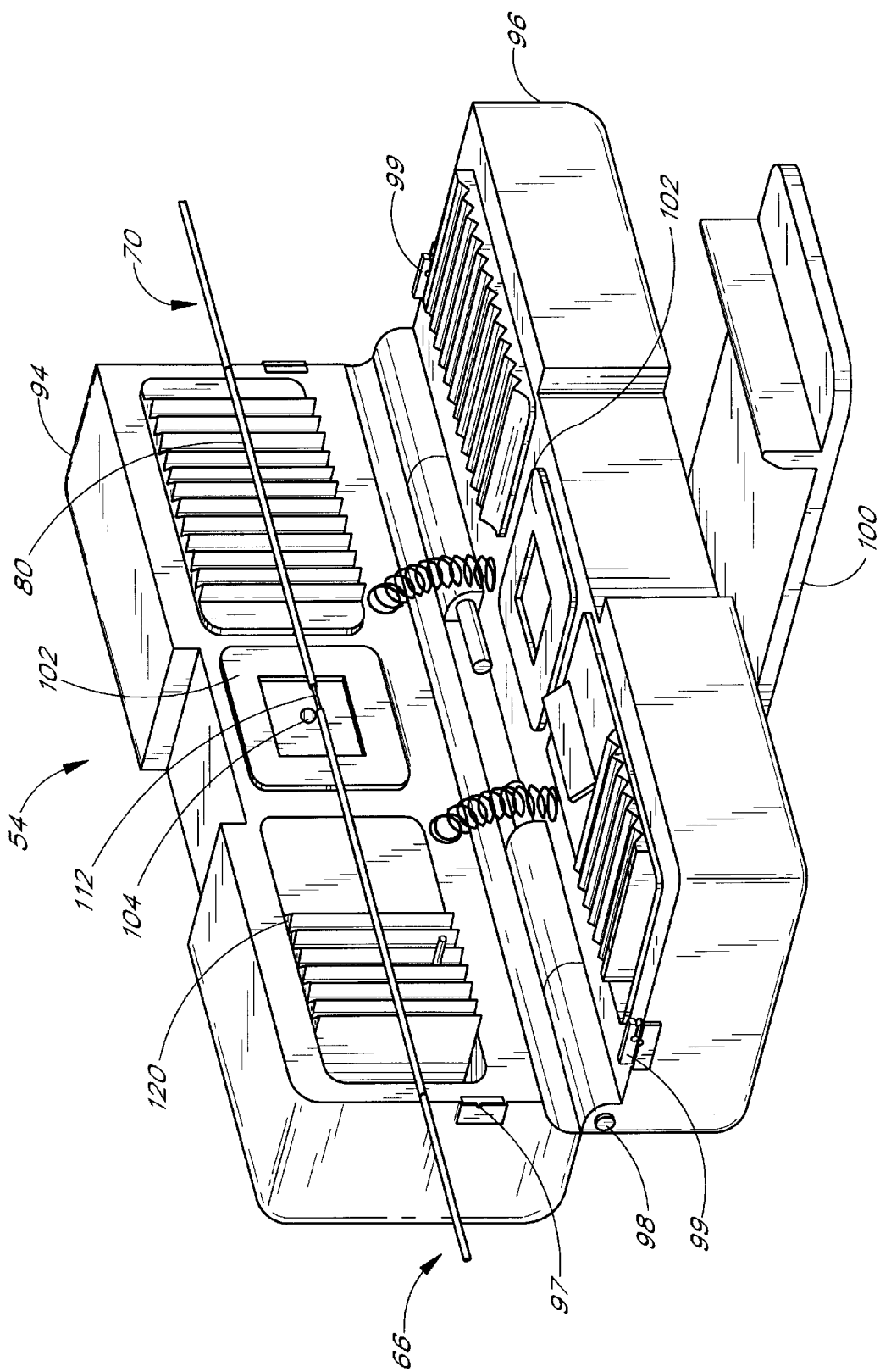
FIG. 8 shows a perspective view of the catheter valve and balloon catheter of FIG. 1 placed within an open inflation adapter.

The catheter valve 66, described in more detail below in connection with FIGS. 7A and 7B, is attached to an open proximal end of the catheter 70. The low volume syringe 60 is used to inject inflation fluid through the adapter 54 and valve 66 into a lumen of the hollow catheter 70, and into the balloon 72. The inflation adapter 54, described in more detail below in connection to FIG. 8, is used to open and close the valve 66 to regulate the inflation of the balloon 72 mounted on the distal end of the catheter 70. Nevertheless, it will be emphasized that other types of adapters and/or valves can be employed with the inflation syringe and/or syringe assembly of the present invention in order to achieve rapid and accurate inflation and deflation of medical balloons or other non-balloon medical devices. Therefore, although the present inflation is illustrated in connection with a low volume occlusion balloon 72, other types of balloons and non-balloon devices can benefit from the advantages of the invention.

The balloon 72 is mounted on a distal end of a hollow guidewire 70 which defines the inflation lumen for the balloon 72, and the syringe 60 and/or syringe assembly 50 is connected at the proximal control end of the guidewire 70. Prior to use of the low volume syringe 60 to inflate the balloon 72 to the proper size for the vascular segment to be treated, the guidewire 70 and balloon 72 are first "primed" or evacuated. The reservoir syringe 62 of the assembly 50 may be used for the evacuation.

B. Occlusion Balloon Guidewire

The occlusion balloon/guidewire system generally illustrated in FIG. 1 performs the function of occluding a vessel and allowing for the slidable insertion or advancement of various other catheters and devices. The term "catheter" as used herein is therefore intended to include both guidewires and catheters with these desired characteristics. The term "occlusion" refers to both partial or total occlusion of a vessel.

As shown in FIG. 2, a balloon guidewire catheter 70 generally comprises an elongate flexible tubular body 80 extending between a proximal control end 82, corresponding to a proximal section of the tubular body 80, and a distal functional end 84, corresponding to a distal section of tubular body 80. Tubular body 80 has a central lumen 86 which extends between ends 82 and 84. An inflation port 90 is provided on tubular body 80 near the proximal end 82. Inflation port 90 is in fluid communication with lumen 86 such that fluid passing through inflation port 90 into or out of lumen 86 may be used to inflate or deflate an inflatable balloon 72 in communication with lumen 86. Further details are disclosed in assignee's co-pending application entitled LOW PROFILE CATHETER VALVE AND INFLATION ADAPTER, application Ser. No. 08/975,723, filed Nov. 20, 1997, the entirety of which is hereby incorporated by reference.

The length of tubular body 80 may be varied considerably depending on the desired application. For example, when the catheter 70 serves as a guidewire for other catheters in a conventional percutaneous transluminal coronary angioplasty procedure involving femoral artery access, tubular body 80 is comprised of a hollow hypotube having a length in the range from about 160 to about 320 centimeters, with a length of about 180 centimeters being optimal for a single operator device, or 300 centimeters for over the wire applications. Alternatively, for a different treatment procedure not requiring as long a length of tubular body, shorter lengths of tubular body 80 may be provided.

Tubular body 80 generally has a circular cross-sectional configuration with an outer diameter within the range from about 0.008 inches to 0.14 inches. In applications where the catheter 70 is to be used as a guidewire for other catheters, the outer diameter of tubular body 80 ranges from 0.010 inches to 0.038 inches and preferably is about 0.014 to 0.020 inches in outer diameter or smaller. Noncircular cross-sectional configurations of lumen 86 can also be adapted for use with the catheter 70. For example, triangular, rectangular, oval and other noncircular cross-sectional configurations are also easily incorporated for use with the present invention, as will be appreciated by those of skill in the art. The tubular body 80 may also have variable cross-sections.

The tubular body 80 has sufficient structural integrity or "pushability" to permit catheter 70 to be advanced through the vasculature of a patient to distal arterial locations without buckling or undesirable kinking of the tubular body 80. It is also desirable for the tubular body 80 to have the ability to transmit torque such as in those embodiments where it may be desirable to rotate the tubular body 80 after insertion into a patient. A variety of biocompatible materials known by those of skill in the art to possess these properties and to be suitable for catheter manufacture may be used to produce the tubular body 80. For example, tubular body 80 may be made of a stainless steel material such as ELGILOY™, or may be made of polymeric material such as PEEK, nylon, polyimide, polyamide, polyethylene or combinations thereof. In one preferred embodiment, the desired properties of structural integrity and torque transmission are achieved by forming the tubular body 80 out of an alloy of titanium and nickel, commonly referred to as nitinol. In a more preferred embodiment, the nitinol alloy used to form the tubular body 80 is comprised of about 50.8% nickel and the balance titanium, which is sold under the trade name TINEL™ by Memry Corporation. It has been found that a catheter tubular body having this composition of nickel and titanium exhibits an improved combination of flexibility and kink resistance in comparison to other materials. Other details regarding construction of catheter 70 may be found in assignee's copending applications entitled HOLLOW MEDICAL WIRES AND METHODS OF CONSTRUCTING SAME, application Ser. No. 08/812,876, filed Mar. 6, 1997, SHAFT FOR MEDICAL CATHETERS, application Ser. No. 09/026,105, filed Feb. 19, 1998, and FLEXIBLE CATHETER, application Ser. No. 09/253,591, filed Feb. 22, 1999, all of which are hereby incorporated by reference in their entirety.

As illustrated in FIG. 2, an expandable member such as an inflatable balloon 72 is mounted on the distal end 84 of the tubular body 80. In one preferred embodiment, the balloon 72 is a compliant balloon formed of a material comprising a block polymer of styrene-ethylene-butylene-styrene (SEBS), as disclosed in assignee's copending application entitled BALLOON CATHETER AND METHOD OF MANUFACTURE, application Ser. No. 09/026,225, filed on Feb. 19, 1998, the entirety of which is hereby incorporated by reference. The balloon 72 may be secured to the tubular body 80 by any means known to those skilled in the art, such as adhesives or heat bonding. For example, for attachment of a SEBS balloon to a nitinol tube, a primer such as 7701 LOCTITE (™) by Loctite Corporation is preferably used along with cyanoacrylate adhesive such as LOCTITE-4011.

The balloon 72 described in the preferred embodiments preferably has a length of about 5 to 9 mm and more preferably about 6–8 mm. Other expandable members are also suitable for the catheter 70, such as those disclosed in assignee's copending application entitled OCCLUSION OF A VESSEL, application Ser. No. 09/026,106, filed Feb. 19, 1998, the entirety of which is hereby incorporated by reference.

With next reference to FIGS. 3A and 3B, a core wire 130 is provided inside the catheter lumen 86. Coils 132 extend from the distal end of the balloon 72, surround the core wire 130, and terminate in a distal ball 134. In one embodiment, the core wire may have one or more tapers, and may extend proximally into tubular body 80. Other details regarding the core wire are disclosed in assignee's copending application entitled CATHETER CORE WIRE, application Ser. No. 09/253,971, filed Feb. 22, 1999, the entirety of which is hereby incorporated by reference.

In one embodiment, as shown in FIGS. 3A and 3B, the tubular body 80 preferably has cuts 140 to create a coiled configuration. A sleeve 142 is preferably provided over the tubular body 80 and the cuts 140 at the proximal end of the balloon 72 to prevent inflation fluid from escaping the lumen 86. Adhesive stops 144 and 146 are provided about 1–2 mm from the ends of the balloon to control the wicking length of the adhesive 148 into the balloon working area. Balloon inflation is provided through the cuts 140 in the tubular body 80. A marker 150 is mounted to the tubular body 80 proximal of the balloon 72. Adhesive tapers 152A, 152B and 154 are provided adjacent the balloon 72 to provide a transition region between the tubular body 80 and balloon 72 at the balloon's proximal end 72A and between the balloon 72 and the core wire 130 at the balloon's distal end 72B. Other details regarding this balloon catheter are described in assignee's above-referenced copending application FLEXIBLE CATHETER.

C. Introducer Arrangement

Figure 4:
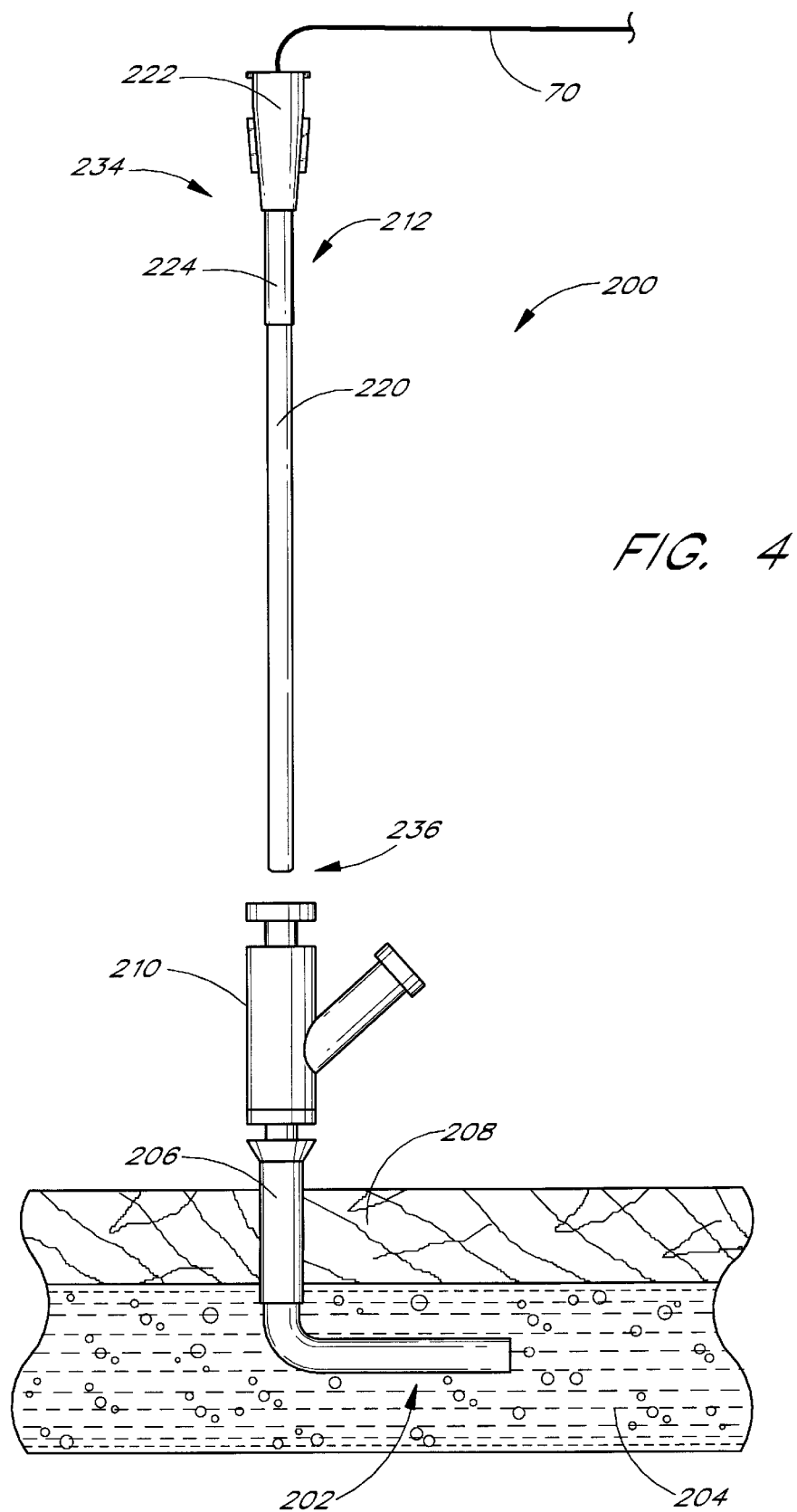
FIG. 4 is a schematic representation of an introducer arrangement including a protective sheath assembly to introduce a catheter with a balloon into a blood vessel.

The catheter 70 and balloon 72 assembly preferably access the vascular site through a port in the patient obtained, for example, using an introducer arrangement 200, as depicted in FIG. 4. As shown, a guide catheter 202 is inserted into a blood vessel 204 through an optional arterial sheath 206. The arterial sheath 206 is inserted into the blood vessel through the skin 208. A Y-adaptor 210 is connected to the proximal end of the guiding catheter 202. A hemostasis valve or a Touhy-Borst valve is installed within the Y-adaptor to prevent blood flow. A protective sheath assembly 212 accommodates the distal end of the catheter 70, including a surgical balloon 72, within the assembly. The protective sheath assembly 212 is then inserted into the Y-adaptor 210 with the distal end of the assembly 212 passing the hemostasis valve mounted in the Y-adaptor 210. As known in the art, the hemostasis valve maintains a tight seal around the protective sheath assembly 212 in order to prevent blood under arterial pressure from bleeding through the valve.

Referring also to FIG. 5, the protective sheath assembly 212 has three major parts: a protective sheath 220, a female luer lock 222, and a strain-relief tubing 224. The protective sheath 220 has an elongated tubular body 226 defining an elongated lumen 230 along a longitudinal axis 232.

The lumen 230 can be further divided into two portions, the proximal portion 230b starting from the proximal end 234 and the distal portion 230a starting from the distal end 236 and extending over a relatively large part of the protective sheath 220.

The dimension of lumen 230 at the proximal portion 230b may vary depending on the outer diameter of the guidewire to be used. The inner diameter and the length of the proximal portion 230b of lumen 230 is designed so that the guidewire can be moved smoothly through the lumen 230 while providing a good seal between the guidewire and the lumen 230 so as to prevent, or minimize, back flow of blood under arterial pressure. The dimension of the distal portion 230a of lumen 230, including the length and the inner diameter, may vary depending on the sizes of the balloon. However, the distal portion 230a should be large enough to accommodate and protect the balloon, as well as the soft tip of a balloon catheter, or other fixed wire devices.

FIG. 6 illustrates a broken side cross-sectional view of the sheath assembly of FIG. 5 and further illustrates, in dotted lines, a catheter 70 positioned within the lumen 230 of the protective sheath 220. Specifically, the catheter 70 comprises a guidewire extending from the proximal end 234 of the sheath 220 and toward the distal end 236. The medical balloon 72, which is mounted on the distal end of the catheter 70, is housed protectively within the distal portion 230a of the sheath 220. It will be noted that the guidewire 70 is housed snugly in the proximal portion 230b of the lumen in order to prevent or at least minimize back blood flow under arterial pressure. The longitudinal position of the balloon is not particularly important so long as it is protectively contained within the lumen 230a.

In a method of the present invention, the proximal end of the guidewire is loaded into the sheath 220 beginning at the distal end 236. This loading is facilitated by a transition section 240, as illustrated in FIG. 5, located between the distal section 230a and the proximal section 230b of the lumen 230. This lumen transition 240 between the proximal portion 230a and the distal portion 230b should be smooth to assist the loading of a balloon guidewire.

Further details and alternative preferred embodiments of introducer arrangements that may be used in conjunction with the present invention are described in assignee's co-pending U.S. application Ser. No. 09/047303, filed on Mar. 24, 1998, entitled MEDICAL WIRE INTRODUCER AND BALLOON PROTECTIVE SHEATH, which is hereby incorporated by reference in its entirety.

D. Low Profile Catheter and Inflation Adapter

Referring again to FIG. 1, the syringe assembly 50 is connected to the occlusion balloon guidewire catheter 70 utilizing an inflation adapter 54. The balloon guidewire catheter 70 has a side-access inflation port 90 and a low profile catheter valve 66 attached to its proximal end (see FIGS. 7A and 7B).

In one embodiment shown in FIGS. 7A and 7B, the low profile catheter valve 66 comprises a movable sealer portion 110 attached at a distal end of a wire segment 112 and positioned within the inflation lumen 86 of the guidewire catheter 70. The wire 112 may be secured to a spring just within a proximal opening of the catheter 70. It will be noted that various spring or biasing arrangements may be utilized, including a zig-zag wire 114 which is formed on or replaces the wire segment 112 and which provides biasing force to the sealer portion 110 due to frictional engagement with the walls of the lumen 86. The sealer portion 110 forms a fluid tight seal with the inflation lumen 86 by firmly contacting the entire circumference of a section of the inflation lumen 86. The sealer portion 110 may be positioned proximally of the side-access inflation port 90 on the catheter as shown in FIG. 7A, to establish an unrestricted fluid pathway between the inflation port 90 and the inflatable balloon on the distal end. As desired, the clinician may move the sealer portion 110 to a position at or distal of the inflation port 90, as shown in FIG. 7B, thereby preventing any fluid from being introduced into or withdrawn from the lumen 86 via the inflation port 90. The valve 66 is considered "low profile" because it is no larger in cross-sectional diameter than the catheter 70 itself. The low profile catheter valve 66 is described in more detail in the above-referenced application LOW PROFILE CATHETER VALVE AND INFLATION ADAPTER.

As discussed above with reference to FIG. 1, the inflation port 90, proximal end of the catheter 70 and distal end of the valve 66 are positioned within the inflation adapter 54 (see FIG. 8), to which the syringe assembly 50 is operably coupled via tubing 64. The syringe 60 is used to inject inflation fluid through the adapter 54 and valve 66 into the lumen 86 of the hollow catheter 70, and into the balloon 72. The inflation adapter 54 is used to open and close the valve 66 to regulate the inflation of the balloon 72.

Referring next to FIG. 8, the inflation adapter 54 comprises a housing having two halves 94, 96 preferably formed of metal, medical grade polycarbonate, or the like. The halves 94, 96 are attached by hinges 98 to be separated or joined in a clam shell manner. A locking clip 100 secures the halves while the adapter 54 is in use. A groove 97 and clips 99 within the housing accept and securely hold the catheter 70 in a correct position. The male luer member 92 (FIG. 1) or another suitable connector, extends from a top of the housing to provide an inflation passageway. Seals 102 are provided within the housing and around an internal segment 104 of the inflation pathway to conduct the pressurized fluid provided by the syringe assembly 50.

An actuator 118, shown in FIG. 1 at the top of the adapter housing 94, controls a cam which operates sliding panels 120 (FIG. 8) contained in the housing. Preferably, the catheter 70 is positioned within the housing with the valve closed (FIG. 7B), such that the side inflation port 90 is located in the sealed inflation area 104 of the housing. The catheter 70 is then positioned in the second half 96 of the adapter 54. A distal portion of the catheter 70 extends out of the housing and into the patient, and a proximal portion of the catheter including the catheter valve 66 extends out of the other side of the adapter 54. The adapter is closed, the locking clip 100 is secured, and the syringe assembly 50 attached. The actuator 118 is moved from a first position to a second position, such that the sliding panels 120 within the housing cause the valve 66 to be in an open position to allow fluid flow through the inflation port 90 (FIG. 7A). The syringe assembly 50 is then used to inflate the balloon 72. Closing the valve 66 is accomplished by moving the actuator 118 from the second position back to the first position (FIG. 7B), such that the balloon inflation is maintained.

Figure 9:
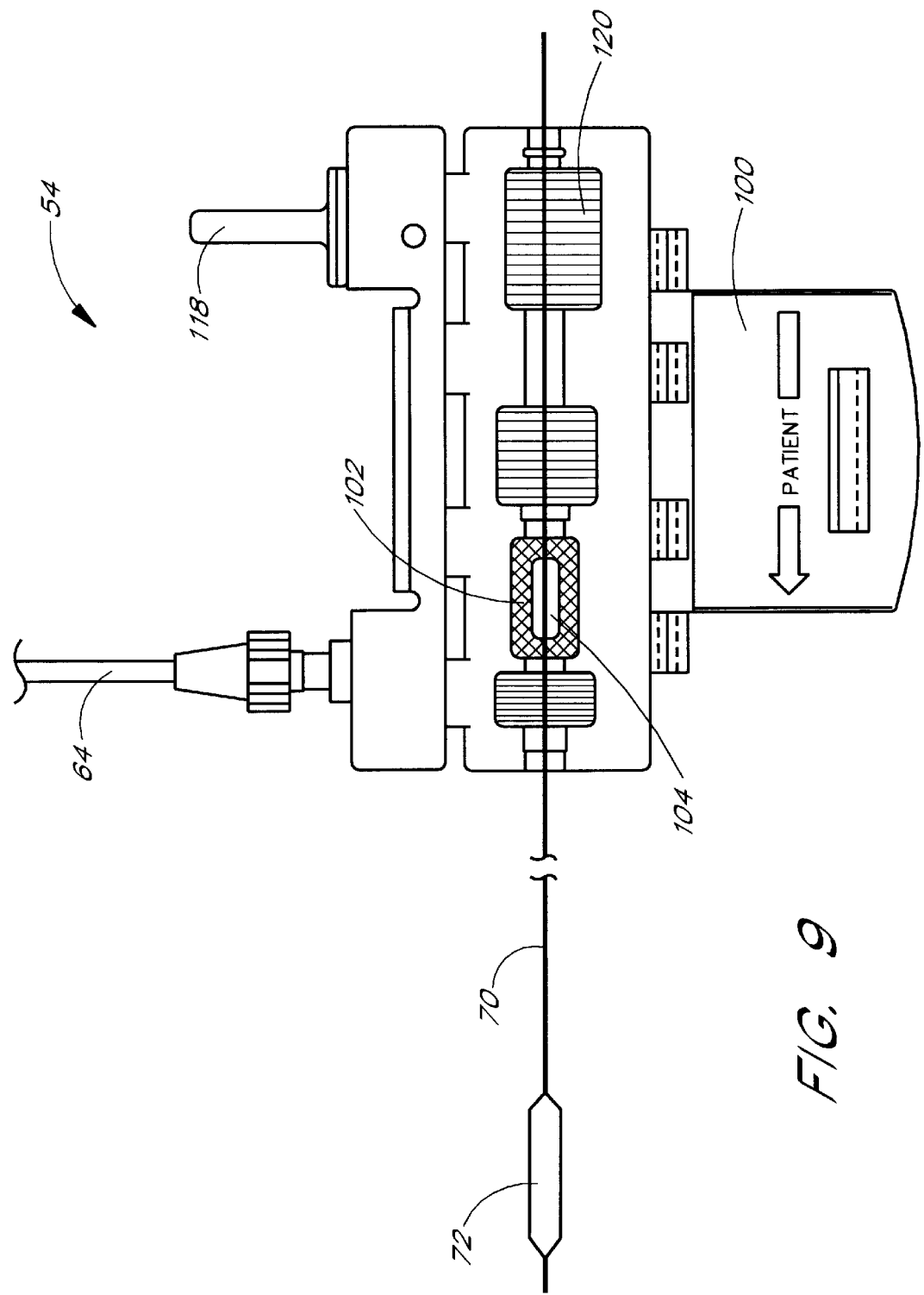
FIG. 9 shows another embodiment of an inflation adapter having a catheter valve and balloon catheter placed therewithin.

Other inflation adapter/inflation syringe assemblies may also be used. For instance, as shown in FIG. 9, the sliding panels 120 and sealer portion 104 of the adapter 54 may be arranged somewhat differently than shown in FIG. 8. Also, the adapter 54 can have additional features, such as a safety lock provided on the actuator knob 70 to prevent accidental opening when the adapter is being used and the catheter valve is open. In addition, the adapter can be provided with an overdrive system to overdrive a sealing member into a catheter. Details of these features and other inflation assemblies may be found in assignee's copending applications LOW PROFILE CATHETER VALVE AND INFLATION ADAPTER, referenced above, SYRINGE AND METHOD INFLATING LOW PROFILE CATHETER BALLOONS, application Ser. No. 09/025,991, filed Feb. 19, 1998, and LOW VOLUME SYRINGE AND METHOD FOR INFLATING SURGICAL BALLOONS, application Ser. No. 09/195,796, filed Nov. 19, 1998, all of which are incorporated by reference in their entirety.

Figure 10:
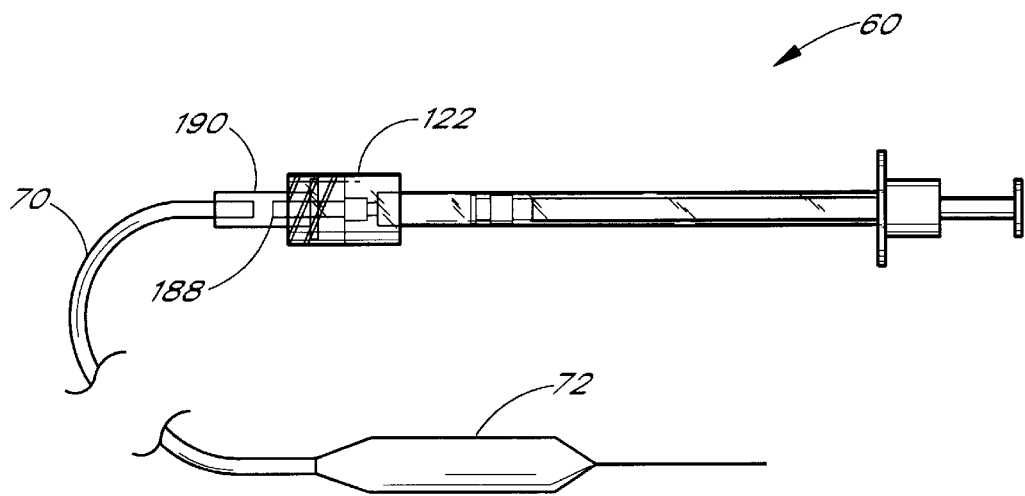
FIGS. 10 and 11 show alternative connections of a low volume syringe having features in accordance with the present invention.
Figure 11:
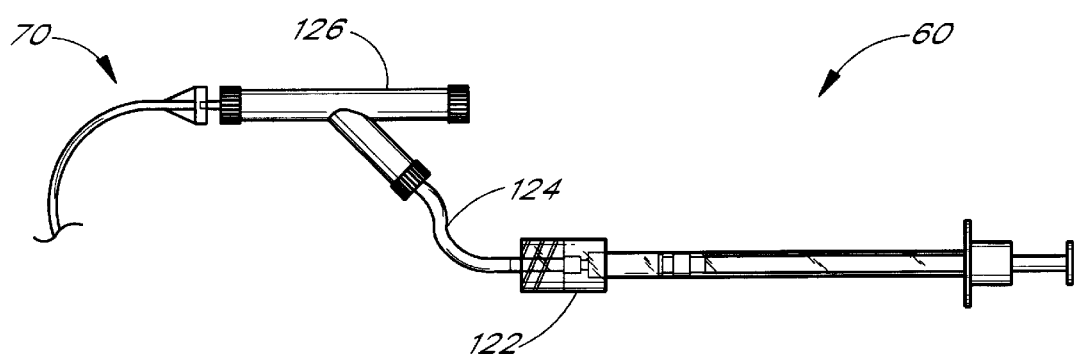

Other connectors or fittings, such as tubing, quick connects and Y-connectors, may also be used in conjunction with an inflation/deflation device having features in accordance with the present invention according to the particular application and available supply of equipment, as shown. In FIG. 10, for example, the inflation syringe 60 is connected via an injection cap 122 directly to the guidewire 70 to allow inflation of the balloon 72 on the catheter. In FIG. 11, the inflation syringe 60 is connected via a short tubing 124 to a connector 126 which is in turn in fluid communication with the catheter 70. Thus, a variety of inflation devices and techniques are available in connection with the inflation syringe 60 of the present invention.

Further details regarding the occlusion system and its use are disclosed in assignee's copending applications entitled ASPIRATION CATHETER, application Ser. No. 09/026, 013, filed Feb. 19, 1998, and EXCHANGE METHOD FOR EMBOLI CONTAINMENT, application Ser. No. 09/049, 712, filed Mar. 27, 1998, both of which are hereby incorporated by reference in their entirety.

II. Low Volume Syringe

Figure 12:
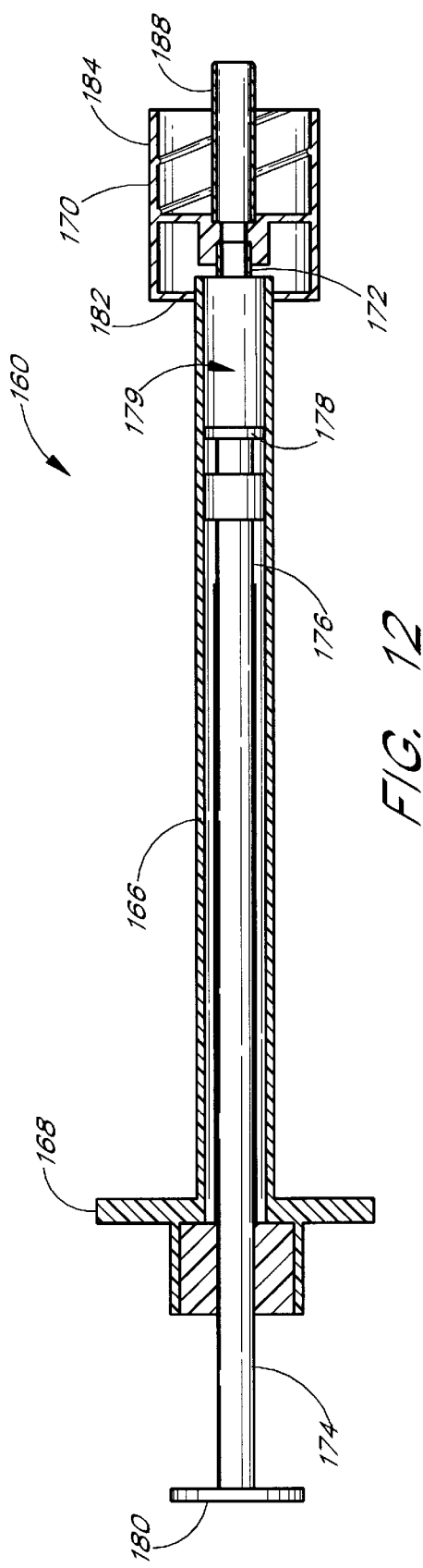
FIG. 12 shows a cross-sectional view along the longitudinal axis of a preferred embodiment of the low-volume syringe of the present invention.

An embodiment of a low volume syringe 60 is shown schematically in FIG. 12. The type or size illustrated is a 0.5 cc tuberculin syringe, although other size syringes having capacity ranging between about 0.02 cc to 1.0 cc may be used. More preferably, the capacity of the low volume syringe is between about 0.25 to 0.50 cc. The resultant displacement required for delivery of about 0.1 cc of fluid is about 10 mm for a 0.25 cc syringe. Indicia 164 may be provided along the length of the exterior surface of a cylinder 166 for visual aid of the clinician during use. Nevertheless, as described below in more detail, a mechanism is advantageously provided on the syringe 160 in order to accurately gauge the inflation fluid intake and expulsion as well as regulate the speed and pressure of fluid injection, thereby providing a means for the clinician to safely and accurately perform the desired procedure.

Figure 13:
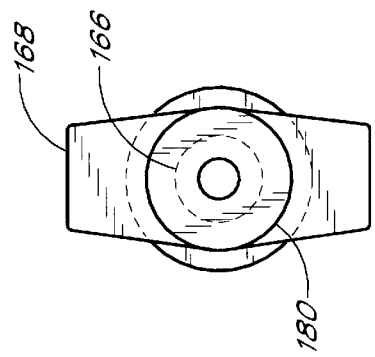
FIG. 13 shows an end view of the low-volume syringe of FIG. 12.
Figure 14:
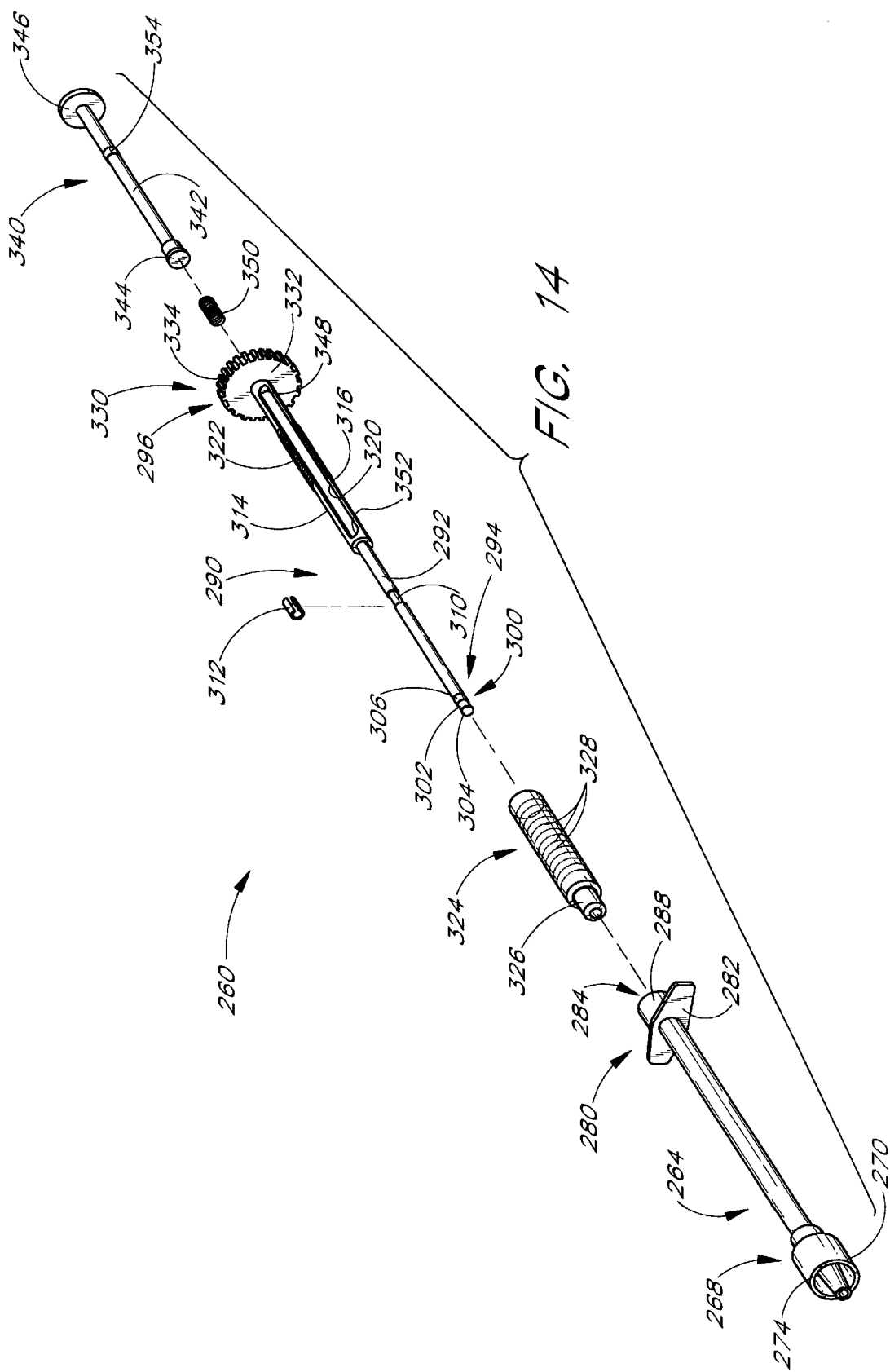
FIG. 14 is an exploded perspective view of a low-volume syringe having features in accordance with the present invention.

Referring to FIGS. 12 and 13, the cylindrical body 166 of the syringe 160 comprises a stop or flange 168 extending radially outward at a proximal end and preferably being attached at a distal end to an injection cap 170. The distal end of the cylinder 166 has a nose portion 172 with a reduced diameter for connection with the injection cap 170.

A plunger 174 has a shaft 176 of appropriate length and a resilient piston 178 attached at its distal end. The shaft 176 is inserted in a central lumen 179 of the cylinder and the piston 178 provides sealing engagement with the inner surface of the cylinder 166. The plunger 174 has a disk 58 at the proximal end of the shaft 176 for operation of the plunger 174. A preferred source for unmodified, conventional syringes is Becton Dickinson & Co. of Franklin Lakes, N.J.

The injection cap 170 preferably comprises a modified female member of a luer type connector. A first end 182 of the cap has a proximal wall with an aperture corresponding to the outer diameter of the cylinder 166, and a distal wall having an aperture corresponding to the outer diameter of the nose 172. These apertures are used to mount the injection cap 170 on the syringe 60. A threaded second end 184 of the cap can be screwed onto a male luer member, as in the example of FIG. 1. Alternatively, a tubular segment 188 within the second end 184 of the cap may be directly attached to the control end of the guidewire 70 using a sleeve 190, as with FIG. 10. Other suitable cap configurations may also be used to facilitate coupling of the syringe to a guidewire or catheter to provide inflation of the balloon. One preferred source of the cap is Medical Disposables International, Inc. of West Conshohocken, Pa.

Another preferred embodiment of the low volume syringe is shown in FIGS. 14–18. The low-volume syringe 260 preferably has a capacity ranging between about 0.1 cc and about 10 cc, and more preferably a capacity between about 0.2 cc and about 2 cc. The syringe 260 includes an elongated hollow body or barrel 264 which is preferably generally cylindrical, but the body can have any desired shape or cross-section. The body 264 has a distal end 268 with an attachment portion 270 which can be connected to various medical components such as a catheter. The attachment portion 270, for example, may include a nose 272, an injection cap 274 and internal threads 276, but it will be understood that the attachment portion can include any type of known connector to attach the syringe 260 to various types of medical components or instruments. The body 264 also includes a proximal end 280 with a flange 282 and an opening 284. The opening 284 is preferably circular and generally aligned with a longitudinal axis extending through the center of the body 264. The stop 282 also includes a radially outwardly extending annular ridge 288. The ridge 288 preferably extends outwardly about 1/16 of an inch from the body 264 and the ridge preferably has a length of about 1/4 of an inch, but the ridge can have any desired dimensions and configuration.

With continued reference to FIGS. 14–18, the syringe 260 includes a plunger 290 which is sized and dimensioned to be at least partially positioned within the elongated body 264. The plunger 290 includes an elongated shaft 292 which is generally circular in cross-section and is preferably constructed from material such as plastic and composites. The plunger 290 includes a distal end 294 which is positioned near the distal end 268 of the body 264 and a proximal end 296 which is positioned near the proximal end 280 of the body. The distal end 294 of the plunger 290 includes a piston 300 with a center section 302 and two outwardly extending annular flanges 304 and 306, respectively. The annular flanges 304 and 306 extend outwardly and slidably engage the inner wall of the elongated body 264 to create a fluid-tight seal with the elongated body. The piston 300 is preferably constructed from a resilient material such as rubber, but it can be constructed from any material which is suitable for its intended purpose. It will be understood that the piston 300 may have any desired size and/or configuration.

The plunger shaft 292 is generally cylindrical and has an annular notch 310 formed therein at a distance from the piston 300 of the shaft. A C-clip 312 is adapted to fit into the notch 310 and is sized to extend annularly outwardly from the shaft 292, effectively creating a ridge encircling the shaft. A length of the shaft near the proximal end is split into two shaft legs 314, 316. A collapsible chamber 320 is defined between the legs 314, 316. Threads 322 are formed about the outer circumference of the legs 314, 316.

A hollow plunger guide 324 has a neck portion 326 formed at its distal end and is adapted to fit complementarily into the proximal opening 284 of the body. The plunger guide 324 is generally cylindrical and has threads 328 formed on its inner surface. The inner threads 328 of the plunger guide 324 are adapted to engage the outer threads 322 of the plunger legs 314, 316 so that the plunger 290 may be threaded within the plunger guide 324. As the plunger 290 is rotated, the threads 322, 328 interact to advance or retract the plunger 290 within the syringe body, depending on the direction of rotation. The inner diameter of the hollow plunger guide's distal neck 326 is less than the diameter of the plunger's clip 312. As such, the C-clip 312 cannot fit through the plunger guide neck 326. Instead, retraction of the plunger 290 from the barrel 264 is stopped when the C-clip 312 contacts the plunger neck portion 326.

Continuing with FIGS. 14–18, the proximal end 296 of the plunger 290 includes a handle 330 comprising a generally circular disk 332 that is mounted to the end of the shaft 292. The disk 332 preferably has ridges 334 formed along an edge thereof, a diameter of about 1 inch, and a thickness of about 1/8 of an inch so that the clinician can easily grasp and rotate the handle 330. However, the disk 332 can be larger or smaller and it can have any desired shape such as square, rectangular, triangular, etc.

Figure 15:
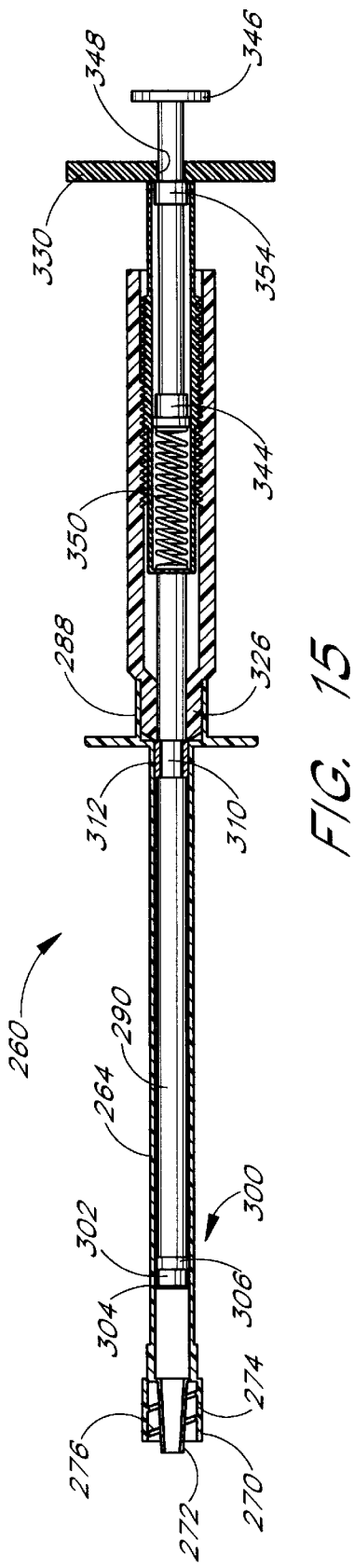
Figure 16:
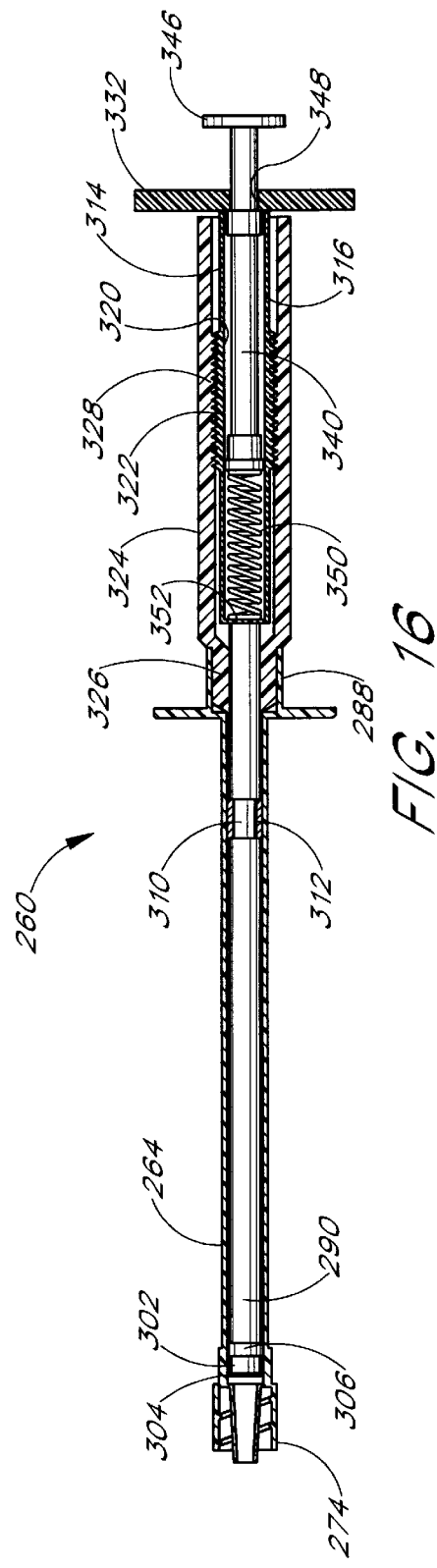

A plunger actuator 340 comprises a shaft 342 with a head 344 formed at its distal end and a tab 346 formed at its proximal end. The plunger actuator shaft 342 is adapted to fit through a hole 348 formed in the handle 330 of the plunger 290 and the head 344 is positioned within the collapsible chamber 320. A spring 350 is disposed within the collapsible chamber 320 between the plunger actuator head 344 and a distal end 352 of the collapsible chamber 320. The spring 350 biases the plunger actuator 340 in a proximal direction. The plunger actuator shaft 342 includes an annular protrusion 354 which contacts the plunger handle 330 to stop the plunger actuator 340 from being pushed by the spring 350 out of the collapsible chamber 320. Thus, the head 344 of the plunger actuator 340 is biased by the spring 350 into a position between the legs 314, 316 of the collapsible chamber 320 about medially between the chamber's proximal and distal ends, as shown in FIGS. 15 and 16. In this position, the head 344 prevents the opposing legs 314, 316 from collapsing toward each other. Thus, the chamber 320 is held in an "open" position.

With particular reference to FIGS. 15 AND 16, when the collapsible chamber 320 is held open by the plunger actuator head 344, the chamber outer threads 322 engage the inner threads 328 of the plunger guide 324. Thus, the plunger 290 can be linearly moved relative to the barrel 264 only by rotating the handle 330. When the handle 330 is rotated in the clockwise direction, the plunger 290 preferably moves toward the distal end 268 of the barrel 264, thus ejecting the contents of the barrel 264 and inflating an associated surgical balloon. When the plunger 290 is rotated in the counterclockwise direction, the plunger 290 is preferably retracted into the barrel 264, thus deflating the balloon.

When the plunger actuator tab 346 is pushed, the plunger actuator 340 compresses the spring 350 and moves the head 344 out of supportive contact with the collapsible chamber legs 314, 316. Thus, as shown in FIGS. 17 and 18, the chamber legs 314, 316 collapse toward each other and the chamber's outer threads 322 move out of engagement with the plunger guide inner threads 328. In this condition, the plunger 290 may be linearly moved relative to the barrel 264 by simply pushing or pulling the handle 330 in the same manner as conventional plungers.

In use, the syringe 260 is preferably first oriented in the open position and the plunger 290 is retracted as shown in FIG. 15. The hollow body 264 between the distal end 268 and the piston 300 is preferably filled with inflation fluid. The handle 330 is then rotated, thus advancing the plunger 290 and delivering the fluid in a regulated, pressure-controlled manner. When the fluid is fully delivered, the syringe 260 is in the position depicted in FIG. 16 and the surgical balloon is inflated.

To quickly deflate the balloon, the plunger actuator 340 is depressed, allowing the chamber 320 to collapse as shown in FIG. 17. While the plunger actuator 340 remains depressed, the clinician pulls on the handle 330, slidably retracting the plunger 290 as shown in FIG. 18.

Figure 19:
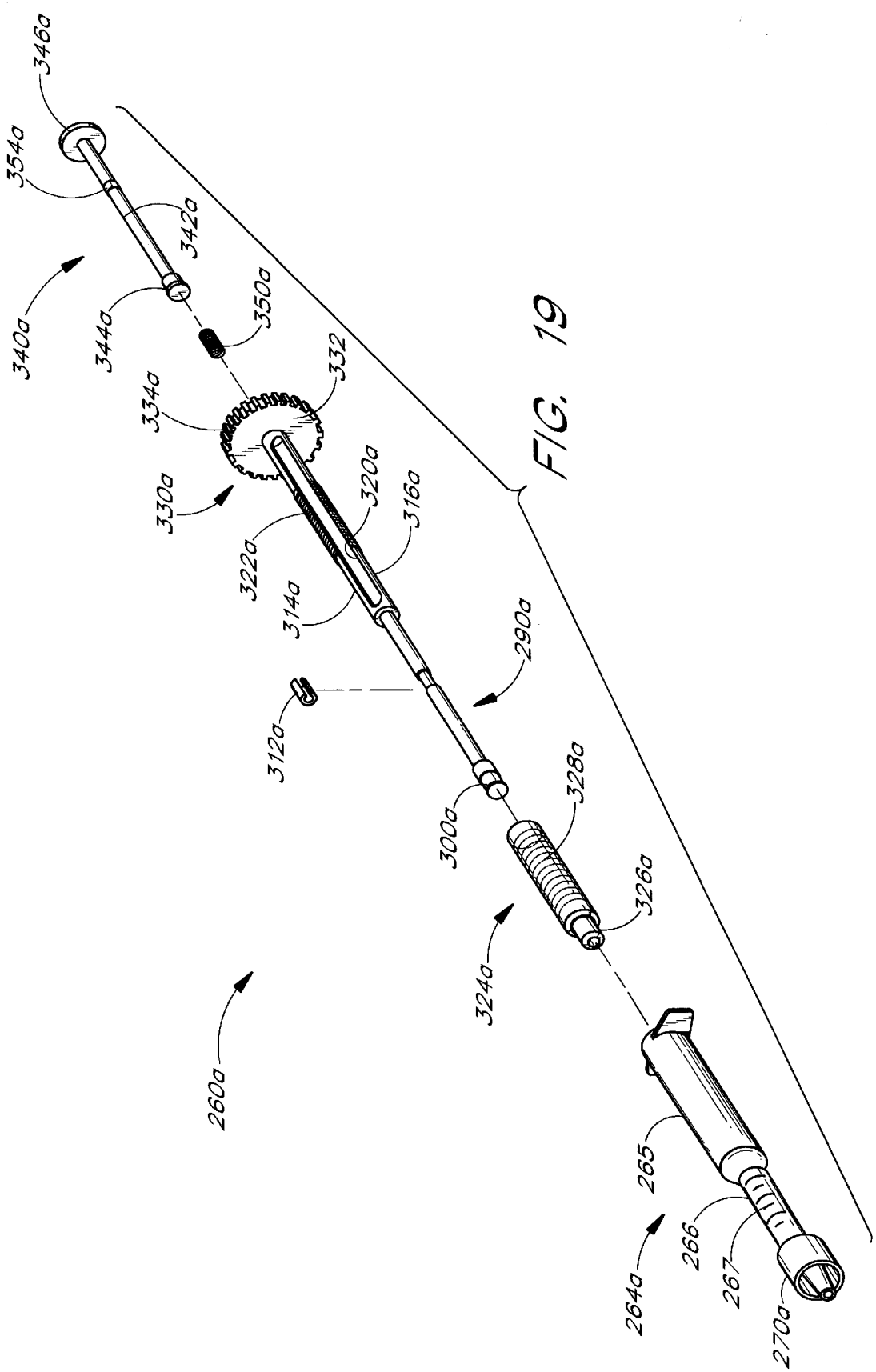
FIG. 19 is a perspective exploded view of another embodiment of an integrated inflation/deflation syringe having features in accordance with the present invention.
Figure 20:
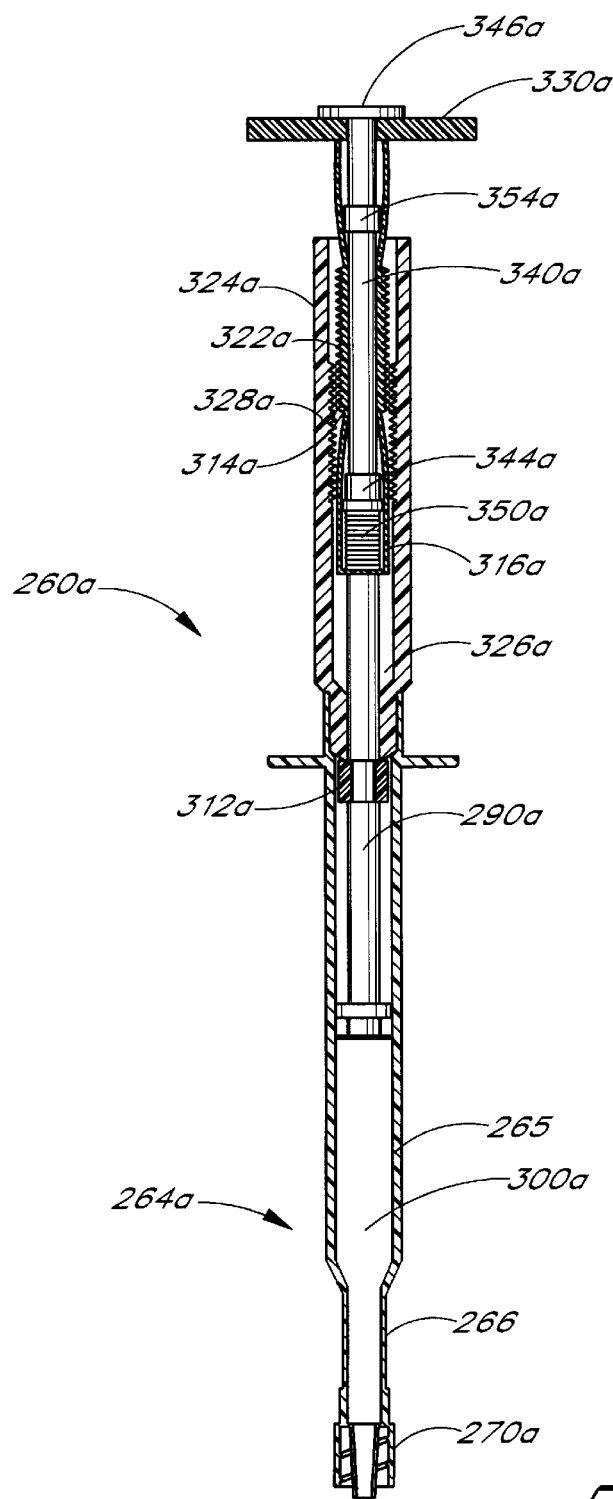
FIG. 20 is a cross-sectional view of the syringe of FIG. 19.

FIGS. 19 and 20 show a preferred embodiment of an integrated inflation/deflation syringe 260a having a variable cross-section barrel 264a. The syringe shares many similarities with the embodiment just discussed and shown in FIGS. 14–18. Thus, similar parts have been assigned the same numbers used above, but including the appellation "a". The similar parts function in substantially the same manner as described above.

With reference to FIGS. 19 and 20, the variable cross-section barrel 264a has a large diameter portion 265 and a small diameter portion 266. The large diameter portion 265 has a cross-section about the same as that of a standard 30–60 cc syringe. The small diameter portion 266 has a cross-section about the same as the low-volume syringe barrel 264 of FIGS. 14–18. The plunger 290a is sized and adapted to slidably fit within the large diameter portion 265 and the piston 300a is sized adapted to effect a seal with the inner surface of the barrel 264a in the large diameter portion 265.

The inflation/deflation syringe 260a is adapted to operate in the same manner as the syringe 260 described above and shown in FIGS. 14–18. Namely, a plunger actuator head 344a supports a collapsible chamber 320a to engage threads 322a on a chamber outer surface with threads 328a on a plunger guide 324a inner surface. The plunger 290a is thus advanced distally within the barrel 264a by rotating a plunger handle 330. Indicia 267 marked on the outside surface of the small diameter section 266 allow the clinician to precisely gauge the volume of liquid delivered by the syringe 260a and the rotational advancement facilitates slow, regulated fluid delivery despite the relatively large size of the barrel 264a in the large diameter portion 265. When the plunger actuator 340a is depressed, moving the head 344a out of supporting contact with the chamber legs 314a, 316a, the chamber 320a collapses. The threads 322a, 328a thus disengage and the piston 300a is free to slide linearly within the barrel 264a. Thus, the plunger 290a may be pulled proximally, rapidly deflating an associated balloon. Because of the relatively large size of the large diameter barrel section 265, the syringe 260a provides powerful evacuation force.

With next reference to FIGS. 21–27, another preferred embodiment of a precision syringe 360 having features in accordance with the present invention is disclosed. With first reference to FIG. 21, the syringe 360 includes a body 364 comprising an elongated hollow barrel 366, a lock body 368, and a correspondingly hollow plunger guide 370. A lumen 372 is defined extending through the hollow body 364 and is preferably circular and generally aligned with a longitudinal axis extending through the center of the body 364. The barrel 366 preferably has a capacity ranging between about 0.1 cc and about 10 cc, and more preferably a capacity between about 0.2 cc and about 2 cc, and has a distal end 378 with an attachment portion 380 which can be connected to various medical components such as a catheter. Referring particularly to FIGS. 22 and 23, the attachment portion 380, for example, may include a nose 382, an injection cap 384 and internal threads 386, but it will be understood that the attachment portion can include any other type of known connector to attach the syringe 360 to various types of medical components or instruments.

Referring again primarily to FIGS. 21–23, a proximal end 390 of the barrel 366 is attached to a distal side 392 of the lock body 368. A proximal side 394 of the lock body 368 is coupled to a distal end 396 of the plunger guide 370, which has a proximal end 398 with a flange or stop 400 formed thereon. The stop 400 includes a radially outwardly extending annular ridge. The ridge preferably extends outwardly about 1/16 of an inch from the body 364 and the ridge preferably has a length of about 1/8 of an inch, but the ridge can have any desired dimensions and configuration.

Figure 21:
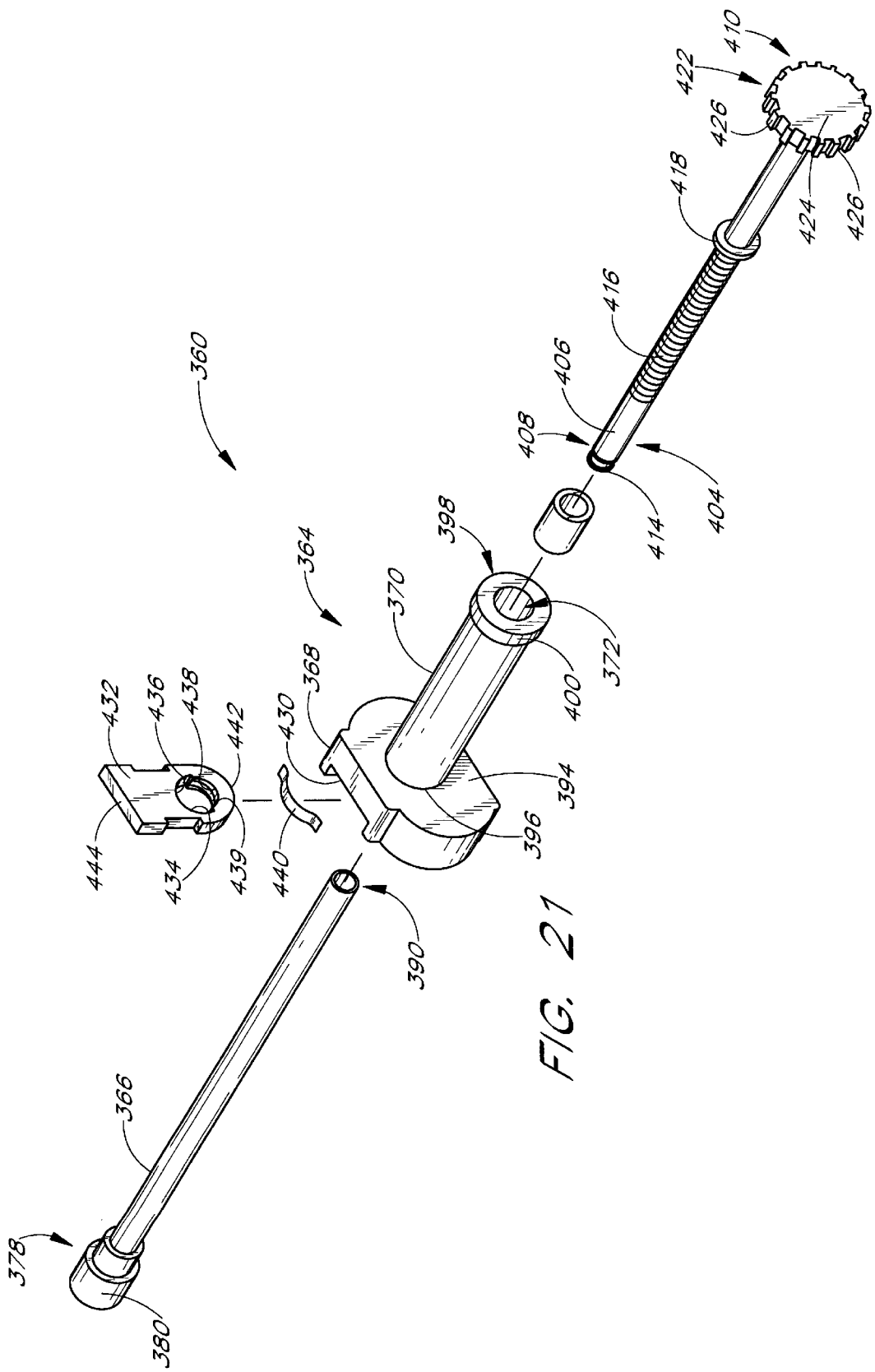
FIG. 21 is an exploded perspective view of yet another embodiment of the low-volume syringe having features in accordance with the present invention.

The syringe 360 also includes a plunger 404 which is sized and dimensioned to be at least partially positioned within the hollow body 364. The plunger 404 includes an elongated shaft 406 which is generally circular in cross-section and is preferably constructed from material such as plastic, metal or composites. The plunger 404 is adapted to fit through the plunger guide 370 and into the barrel 366 and includes a distal end 408 which is positioned near the distal end 378 of the barrel, and a proximal end 410 which is positioned near the proximal end 398 of the plunger guide 370 as shown in FIGS. 21 and 23. The distal end 408 of the plunger 404 includes a piston 414 which is adapted to form a seal between the piston 414 and the inner surface of the barrel 366, as above. The plunger shaft 406 is threaded 416 from a point near the distal end 408 to a plunger stop 418. The stop 418 comprises an annular ridge extending outwardly about 1/16 inch from the shaft. A guide ring 420 within the plunger guide 370 helps stabilize the plunger 404 within the guide. As shown in FIG. 19, the stop 418 on the plunger 404 contacts the plunger guide flange 400 to prevent further distal advancement of the plunger 404.

Referring again to FIG. 21, the proximal end 410 of the plunger 404 includes a handle 422 comprising a generally circular knob 424 with ridges 426 formed around the perimeter thereof to facilitate rotational grip by the clinician. The knob 424 preferably has a diameter of about 1 inch and a thickness of about 1/8 of an inch so that the clinician can easily grasp it, but the knob can be larger or smaller and it can have any desired shape such as square, rectangular, triangular, etc.

Figure 24:
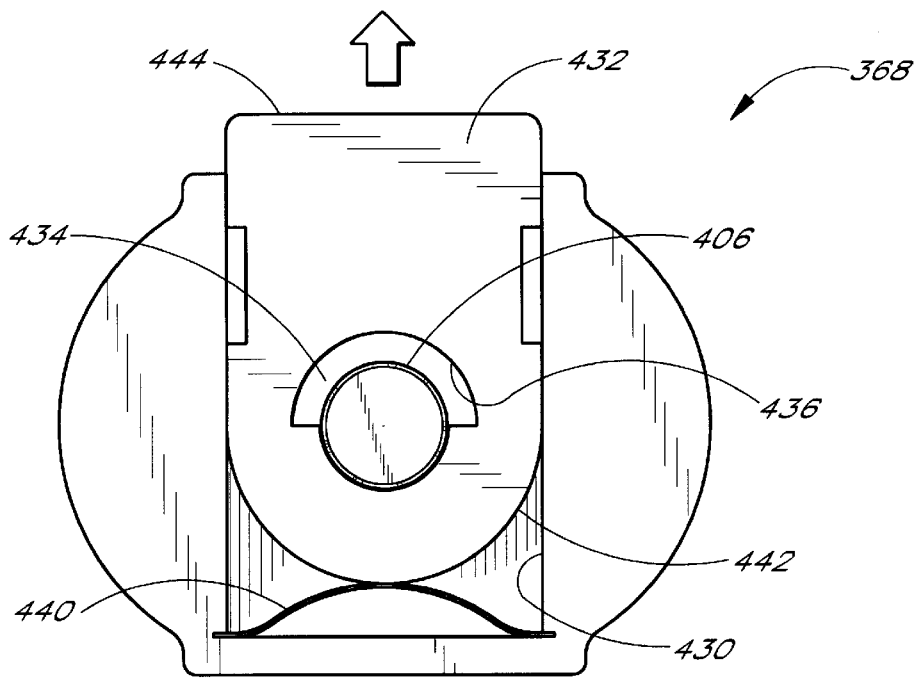
FIG. 24 is a plan view of a lock body installed on the syringe of FIG. 21, showing a lock tab in a thread-engaging position.
Figure 25:
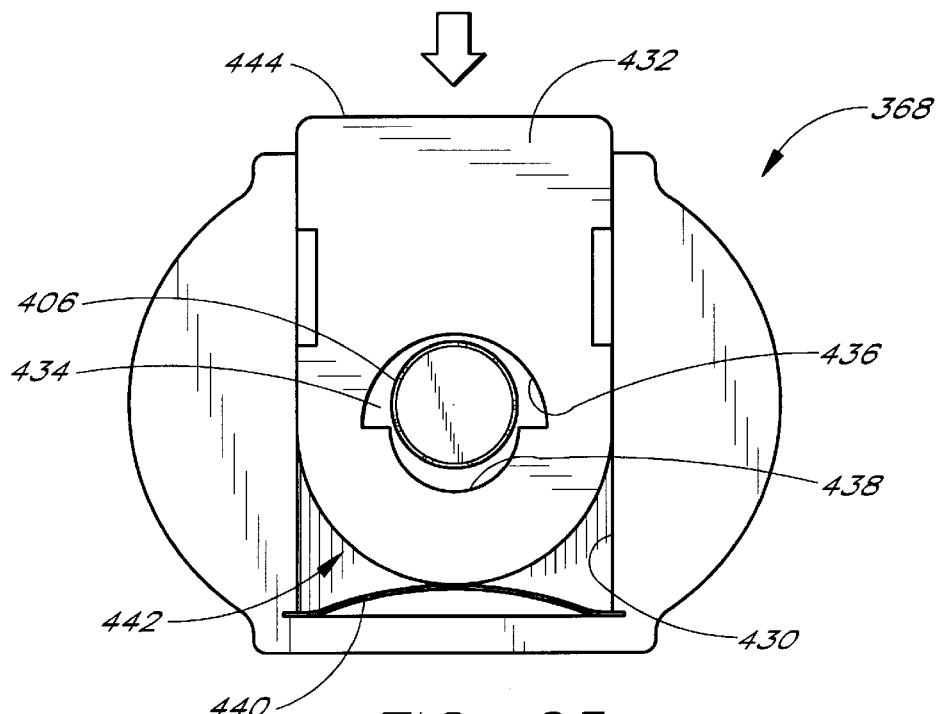
FIG. 25 is a plan view of the lock body of FIG. 28, showing the lock tab in an unlocked position relative to the plunger.

With further reference to FIGS. 24 and 25, the lock body 368 has a slot 430 which is adapted to receive a locker tab 432 therein. A hole 434 extends through the locker tab 432 and has an upper portion 436 and a lower portion 438. The radius of curvature of the upper portion 436 is larger than that of the lower portion 438, which is threaded 439 (see FIG. 21) to match the threads 416 on the plunger 404. A spring 440 such as a parabolic spring or coiled spring is disposed in the lock body slot 430 in contact with a curved leading edge 442 of the tab 432 and biases the locker tab 432 away from the spring 440. When the plunger 404 is inserted into the syringe body 364, the spring 440 biases the locker hole threads 439 into contact with the plunger threads 416, as shown in FIGS. 22–24. Thus, to advance or retract the plunger 404, the knob 424 must be rotated so that the plunger 404 is threaded into or out of the body 364. In this manner, precise volumes of liquid may be delivered out of the plunger barrel 366 in a regulated, relatively slow manner. Thus, build-up of excessive pressure in the occlusion system will be avoided because the plunger 404 will not be advanced too quickly down the barrel 366 when ejecting the barrel's contents.

Figure 26:
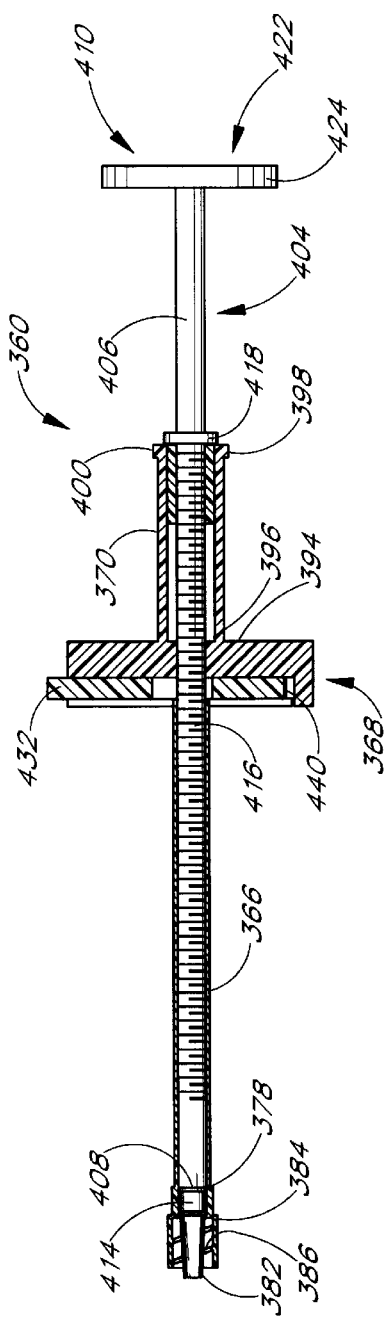
FIGS. 26–27 are cross-sectional views of the syringe of FIG. 21, showing the plungers disengaged from the thread tab.
Figure 27:
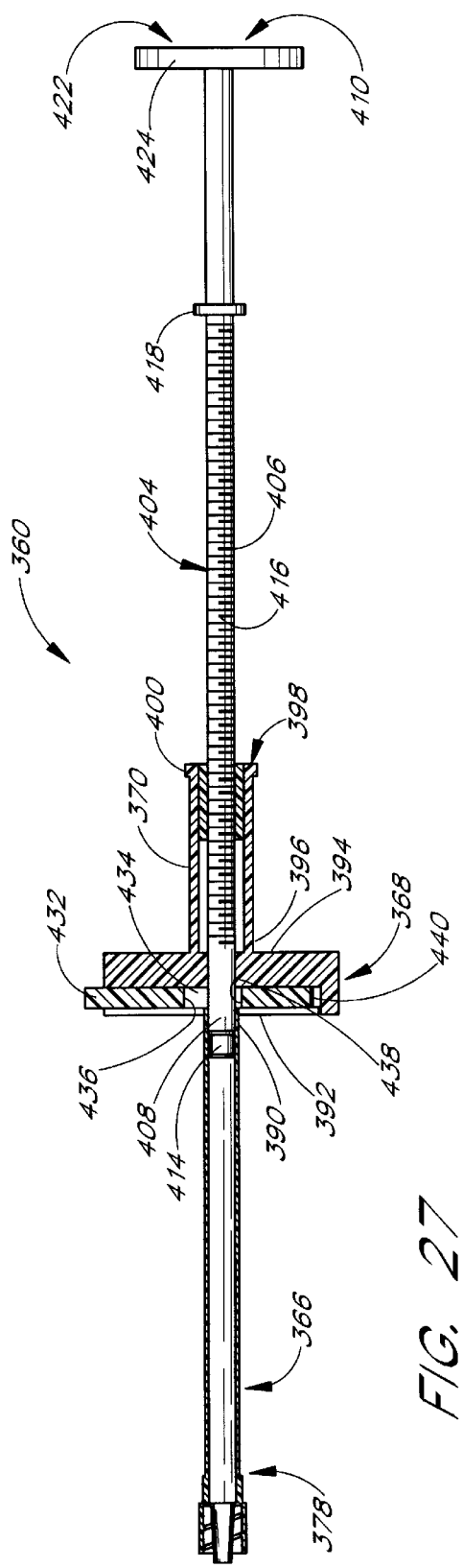

When a back edge 444 of the locker tab 432 is depressed, as shown in FIGS. 25–27, the locker threads 439 are taken out of engagement with the plunger threads 416. The plunger 404 is thus free to be slidably moved without resistance from threads. Thus, the plunger knob 424 can be pushed or pulled to rapidly slide the plunger 404 within the barrel 366. This arrangement is especially desirable to enable quick deflation of an occlusion balloon.

The above preferred embodiment enables precise regulated injection of liquid when the plunger 404 is rotated, thus delivering the contents of the barrel 366 slowly and avoiding over pressurizing a connected occlusion system. However, when the lock tab 432 is depressed, the syringe 360 allows rapid deflation of the associated balloon.

FIGS. 28–32 show another preferred embodiment of a syringe 460 having features in accordance with the present invention. The syringe 460 is adapted to inflate an occlusion balloon by delivering precise volume of liquid in a regulated, low pressure manner that will not cause leaks in a system and also to deflate the occlusion balloon quickly.

With reference first to FIG. 28, the syringe 460 comprises a hollow body 464 with a barrel 466 extending from a distal end 468 of the body 464. The majority of the body 464 has a greater diameter than the barrel 466, which preferably has a capacity between about 0.1 cc and 10 cc, and more preferably between about 0.2 cc and 2 cc. The barrel 466 has a distal end 469 with an attachment portion 470 which can be connected to various medical components such as a catheter. The attachment portion 470 may include, for example, a nose 472, an injection cap, and internal threads, but it will be understood that the attachment portion can include any type of known connector to attach the syringe 460 to various types of medical components or instruments.

A plunger 480 is disposed within the body 464 and barrel 466 and comprises a shaft 482 with a piston 484 attached to a distal end thereof. The piston 484 is adapted to form a seal between the piston 484 and the inner surface of the barrel 466, as above. A shuttle 490 is attached to a proximal end 492 of the plunger shaft 482 and is slidably disposed within the main body 464. With further reference to FIG. 29, the shuttle 490 has a chamber 494 formed therewithin and an opening 496 to the chamber 494 is formed at a proximal end 498 of the shuttle 490. The chamber 494 is preferably substantially cylindrical and has a proximal neck portion 500 surrounding the opening 496 and having a diameter less than the diameter of the majority of the chamber 494.

Referring again to FIGS. 28–31, a plunger actuator 502 is provided which comprises a shaft 504 having a distal end 506 which is disposed in the shuttle chamber 494 and a proximal end 508 which extends out of a proximal end 510 of the body 464 and on which a handle 512 is formed. The handle 512 preferably comprises a generally circular disk 514 with a diameter of about ⅞ of an inch and a thickness of about ⅛ of an inch so that the clinician can easily grasp it. However, the disk can be larger or smaller and it can have any desired shape.

An annular stop ridge 518 is formed on the distal end 506 of the plunger actuator 502. The ridge 518 is sized and adapted to slide freely within the chamber 494, but has a diameter greater than that of the chamber neck 500 and will not fit through the opening 496. Therefore, the stop ridge 518 prevents the plunger actuator 502 from being completely removed from the shuttle chamber 494.

The proximal end 498 of the shuttle 490 has a flat surface on which a distal end 520 of a coil spring 522 rests. The spring 522 encircles the plunger actuator shaft 504 and extends proximally to a spring stop ridge 524 which protrudes annularly from the shaft 504.

Figure 32:
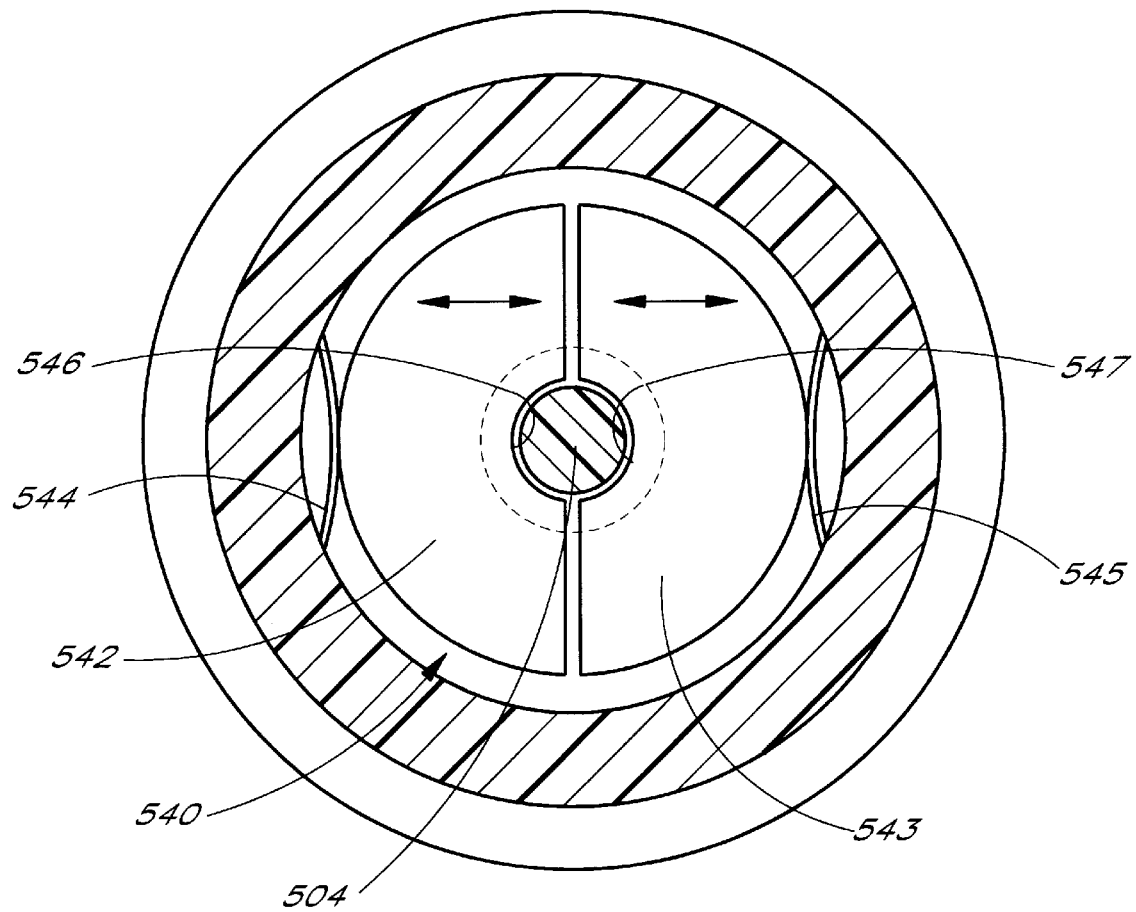
FIG. 32 is an end view of a detent mechanism for use with the syringe of FIG. 28.

Referring more particularly to FIGS. 28 and 30, the proximal end 510 of the body 464 has a flange 526 formed thereon. A hollow detent cylinder 530 extends longitudinally from the body flange 526. A cover 532 is disposed on a proximal end of the detent cylinder 530 and has an opening 536 formed therethrough. A detent mechanism 540 is disposed within the detent cylinder 530. With further reference to FIG. 32, the detent mechanism 540 preferably comprises opposing tabs 542, 543 linearly movable in a direction generally perpendicular to the body 464 and biased toward each other by springs 544, 545. A cavity 546, 547 is formed in each tab 542, 543, respectively, and is adapted to closely surround the plunger actuator shaft 504. With reference to FIGS. 28 and 30, a detent ridge 548 protrudes annularly from the plunger actuator shaft 504 between the spring stop 524 and the handle 512. A distal surface 550 of the detent ridge 548 is preferably sloped at about a 45° angle relative to the detent tabs 542, 543. The sloped distal surface 550 is adapted to deflect the detent tabs 542, 543 when the detent ridge 548 passes between them, thereby facilitating easy passage of the detent ridge 548 through the detent mechanism 540. A proximal surface 552 of the detent ridge 548 is also sloped, preferably at an angle relative to the detent tabs 542, 543 of about 15–40° and most preferably about 30°. The sloped proximal surface 552 is also adapted to deflect the tabs 542, 543 to facilitate passage of the detent ridge 548 through the detent mechanism 540, but due to the slope angle, significantly more force is required to move the detent ridge 548 proximally through the tabs than distally through the tabs.

This arrangement is particularly useful when operating the syringe 460. As shown in FIG. 30, when the disk 514 is pushed downward so that the detent ridge 548 passes through the detent mechanism 540, the spring 522 is compressed against the shuttle 490 and the distal end 506 of the plunger actuator 502 approaches a distal end 554 of the shuttle chamber 494. When compressed, the spring 522 exerts a reaction force F on the spring lock 524 and the shuttle 490. The spring 522 is adapted to not generate enough spring force F to push the detent ridge 548 proximally through the detent mechanism 540. Therefore, the spring force F instead tends to move the shuttle 490 in a distal direction, thus advancing the plunger 480 toward the barrel's distal end 469 until the contents of the barrel 466 are delivered and the spring 522 is relaxed, as shown in FIG. 31.

An advantage of the present embodiment is regulation of pressure build-up in the occlusion system. As discussed above, when liquid is injected too quickly into the system, pressure may build to very high levels and cause leaks in the system. The present embodiment allows a clinician to not worry about the rate of entry of liquid into the system. Instead, the clinician simply depresses the tab 514 until the detent ridge 548 is engaged with the detent mechanism 540. The spring 522 is thus compressed as shown in FIG. 30. As discussed above, the spring exerts force F to move the shuttle 490 and plunger 480 distally within the body 464, delivering the contents of the barrels 466 to the occlusion system. However, the spring 522 is chosen to have a spring constant adapted to exert a force less than the pressure that would cause a leak in the system. Thus, the spring 522 will inherently regulate system pressure during fluid delivery.

To deflate the occlusion balloon, the clinician pulls the plunger actuator 502 proximally, preferably moving the plunger 480 from the position depicted in FIG. 27 to the position shown in FIG. 25. The pulling force of the clinician is sufficient to move the detent ridge 548 through the detent mechanism 540 and the plunger actuator stop ridge 518 contacts the shuttle neck 500 so that the shuttle 490, and thus the plunger 480, moves proximally with the plunger actuator 502. Thus, the contents of the catheter are drawn into the barrel 466 and the balloon is deflated quickly.

III. Inflation Syringe and Balloon Sizing System

To accommodate a variety of vessel sizes, various sizes of occlusion balloons are typically used. For example, balloon diameters of 3.0 mm, 3.5 mm, 4.0 mm, 4.5 mm, 5.0 mm, 5.5 mm, and 6.0 mm are common. Balloons with diameters of 2.0 mm, 2.5 mm and 7.0 mm are also useful. Prior systems required different inflation devices to be used in combination with each of the balloon sizes. Further details are provided in the above-referenced copending application SYRINGE AND METHOD FOR INFLATING LOW VOLUME CATHETER BALLOONS. Improvements in balloon technology have resulted in at least one system in which a single balloon is suitable for use in a number of different vessel diameters. These improvements are disclosed in the above-referenced copending U.S. Application BALLOON CATHETER AND METHOD OF MANUFACTURE.

A single syringe may be used to provide inflation fluid to the balloon. If desired, the syringe may be marked with indicia along its barrel to assist the physician during inflation of the balloon. The indicia are adapted to enable precise delivery of low volumes of fluid, but also versatile enough to enable accurate delivery of a range of volumes. For example, a 2.0 mm diameter balloon may be able to accommodate only about 0.01 cc of inflation fluid and a 7.0 mm balloon may require about 0.25 cc of fluid.

IV. Syringe Assembly

In the embodiment of FIG. 1, an inflation syringe 60 is depicted used in an assembly 50 including a conventional high capacity or reservoir syringe 62. The reservoir syringe 62 provides the desirable power and volume for quickly priming the balloon 72 and guidewire 70, as well as for quickly deflating the balloon 72 for withdrawal from the patient. However, it will be noted that the inflation syringe 60 can be utilized in combination with other reservoir systems, of which the assembly 50 is only one example. Also, any of the preferred syringe embodiments disclosed above can be utilized in combination with such a reservoir syringe 62 or other reservoir systems.

Figure 33:
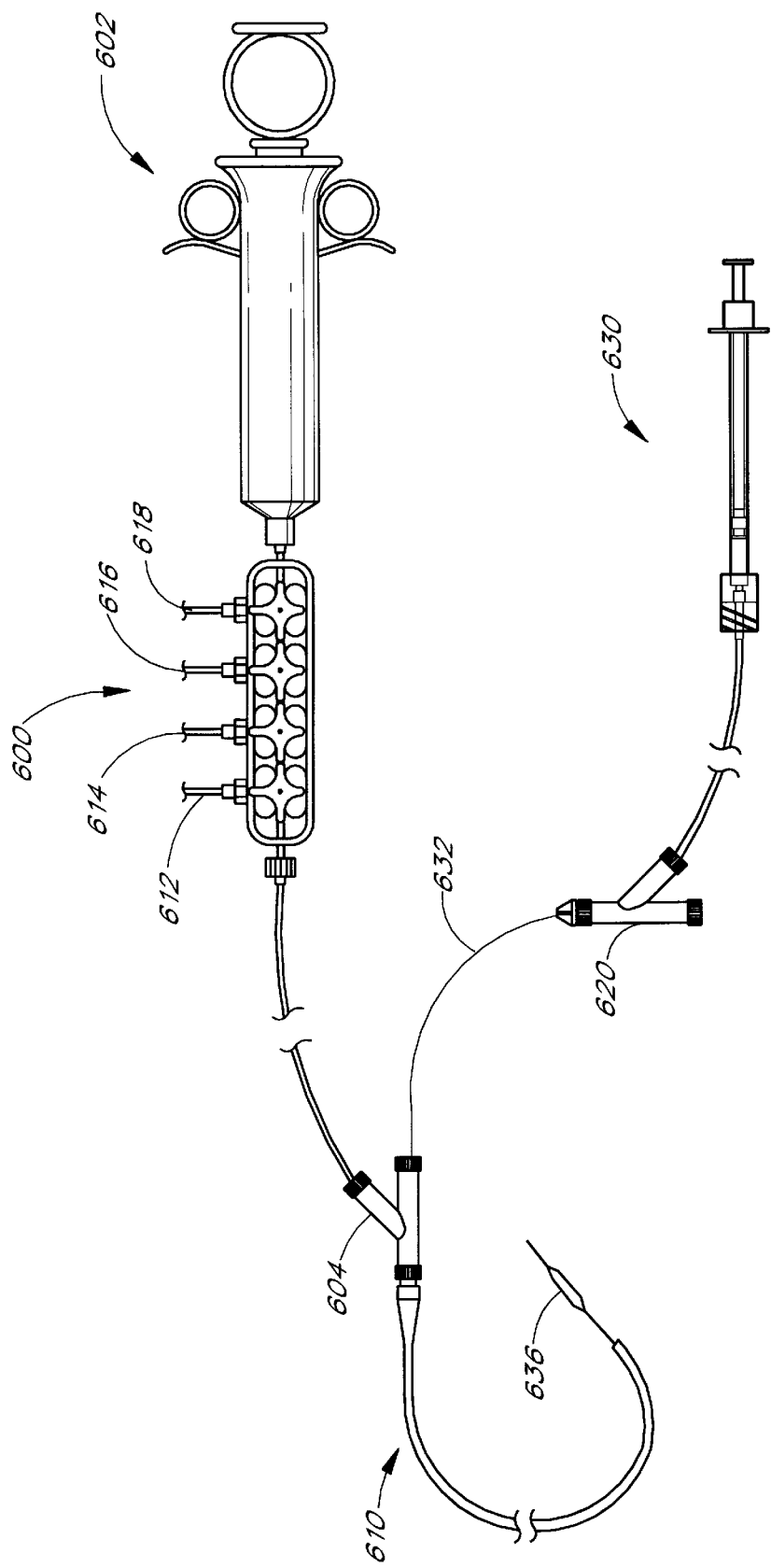
FIG. 33 shows an alternative syringe assembly.
Figure 34:
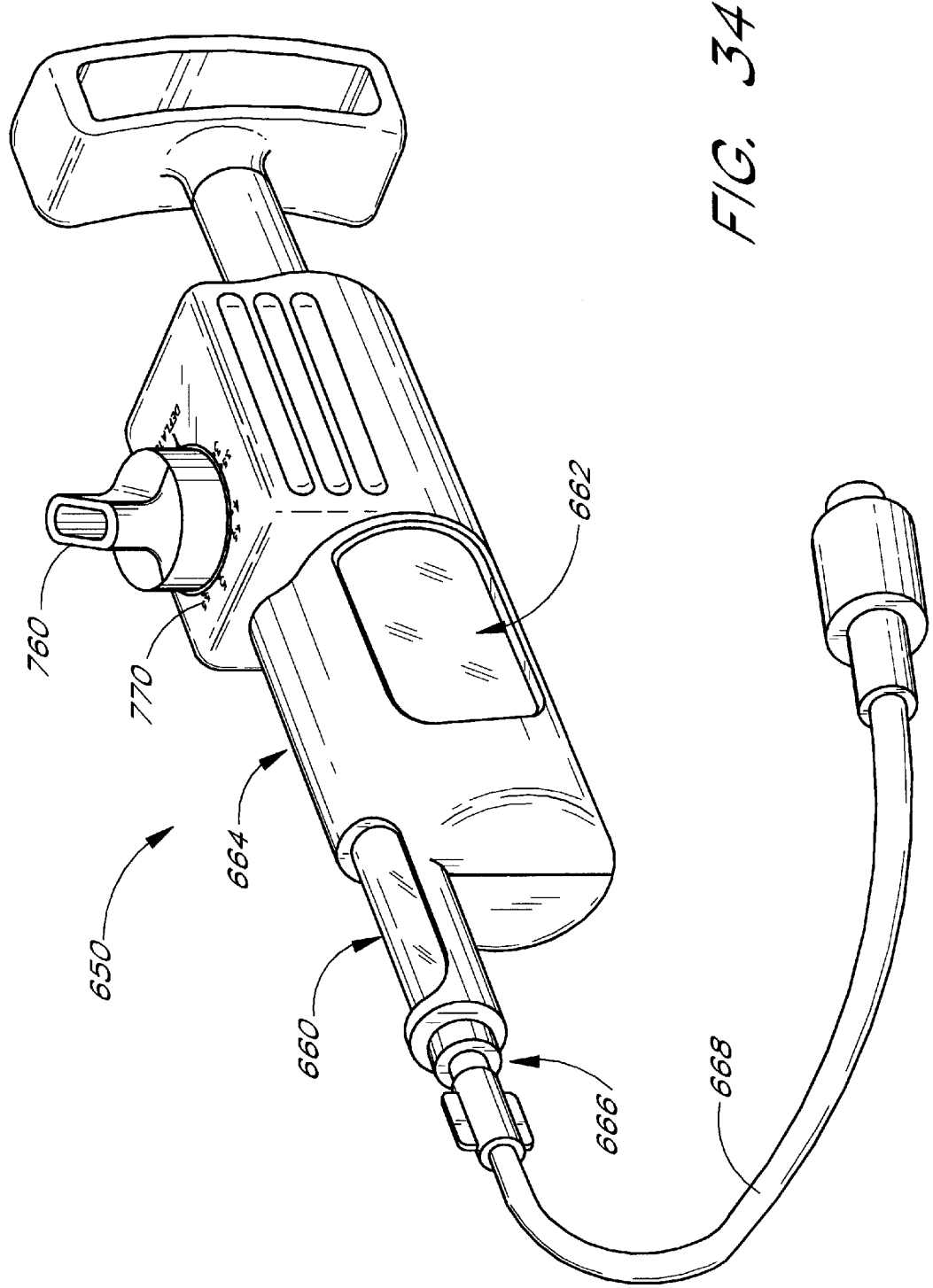
FIG. 34 is a perspective view of a preferred embodiment of an integrated inflation/deflation device having features in accordance with the present invention.

An alternative syringe assembly is shown in FIG. 33, wherein a conventional four-way manifold 600 is attached to a reservoir syringe 602 and a y-connection 604 is attached to the proximal end of a catheter 610. The manifold 600 provides a pressure monitoring line 612, a dye supply line 614, a saline supply line 616, and a waste removal line 618. Proximal this first connection 604, another y-connection 620 couples a low volume syringe 630 with a guidewire 632 and, thus, with the manifold 600 and reservoir syringe 602. The syringe 630 is used to inflate the distal balloon 636 on guidewire 632. Although the use of a manifold 600 is typically reserved for procedures using larger or therapeutic balloons, those skilled in the art will appreciate that the present invention is readily adapted for use with this more elaborate system.

As understood by those skilled in the art, the assembly in the present invention is not limited to the embodiments discussed herein, and may be included with other adapters, manifolds, and/or connectors, as desired. That is, advantages realized from the use of the low volume syringe with the higher volume syringe for deflation and inflation of a balloon during various procedures is not limited to their particular connections or additional apparatus.

Figure 35:
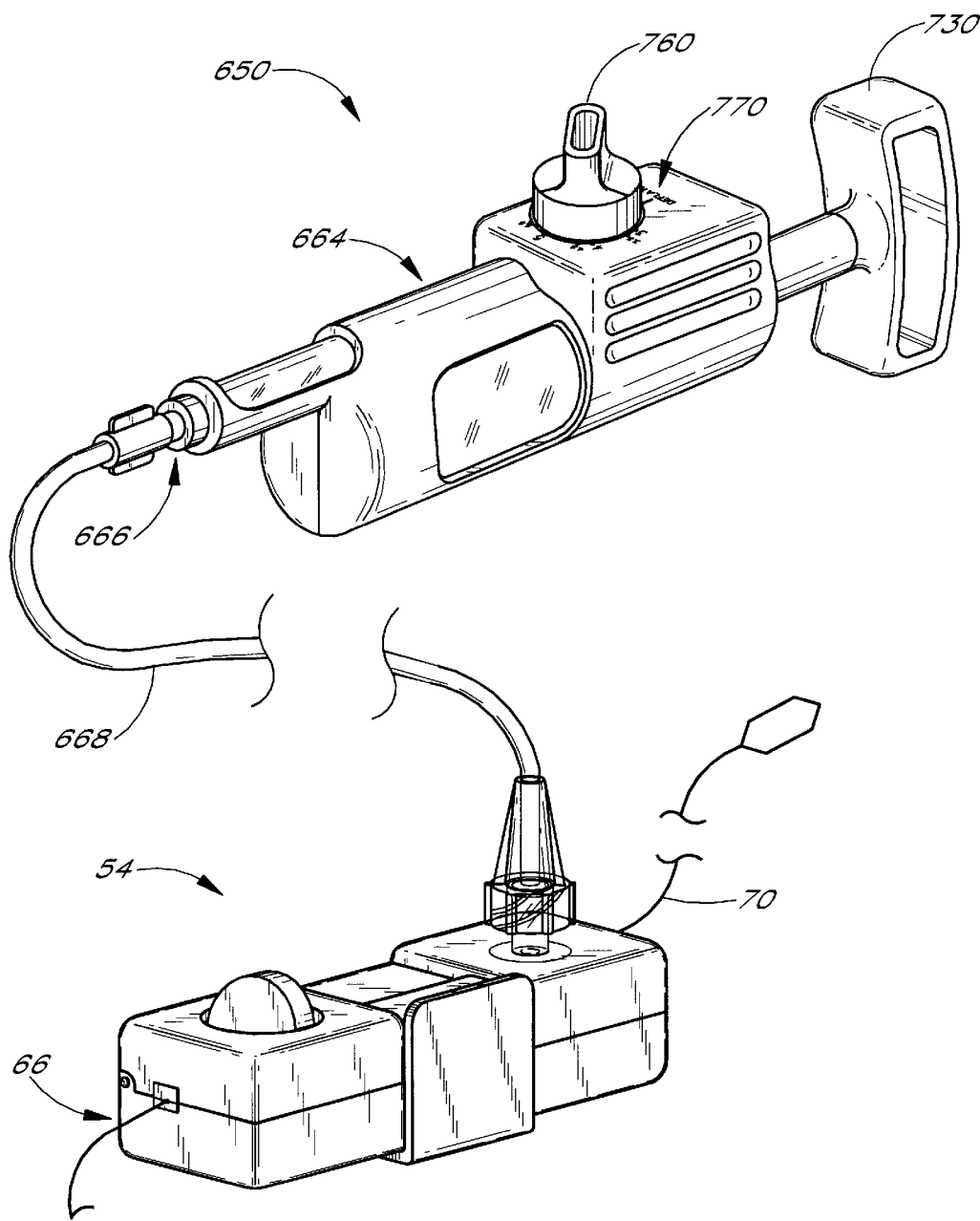
FIG. 35 is a perspective view of the device of FIG. 34, shown operably coupled to an illustrative inflation adapter and a proximal portion of a balloon catheter.

Another preferred embodiment of a syringe assembly 650 for inflation and deflation of an occlusion balloon is shown in FIGS. 34–44. With first reference to FIG. 34, the syringe assembly 650 comprises a low-volume inflation syringe 660 and a high capacity or reservoir syringe 662 encased together in a housing 664. Like the syringe assembly 50 shown in FIG. 1, and as illustrated in FIG. 35, the syringe assembly 650 is preferably attached via a connector 666 and a short tube 668 to an adapter 54 within which a low profile catheter valve 66 and a balloon catheter 70 are engaged during use.

Figure 36:
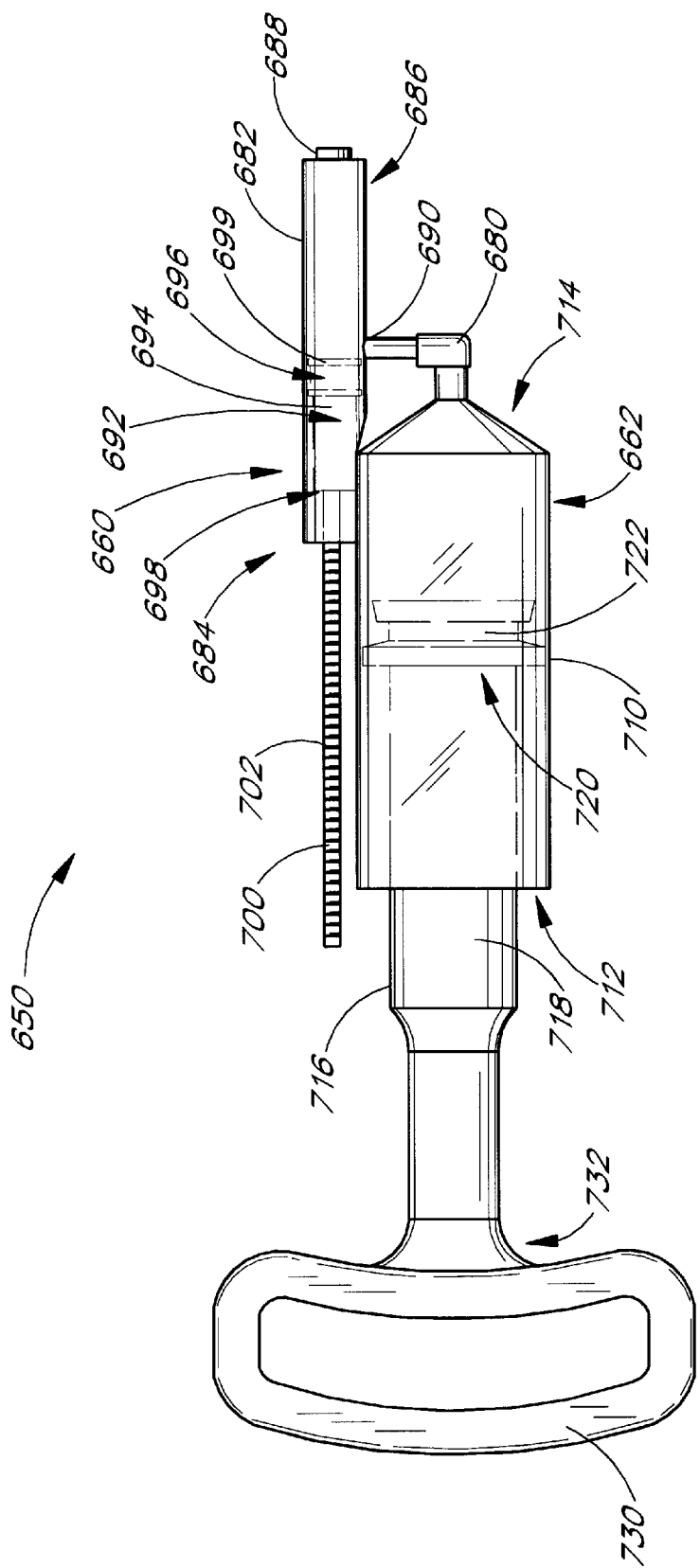
FIG. 36 is a side view of a syringe assembly portion of the device of FIG. 34.
Figure 37:
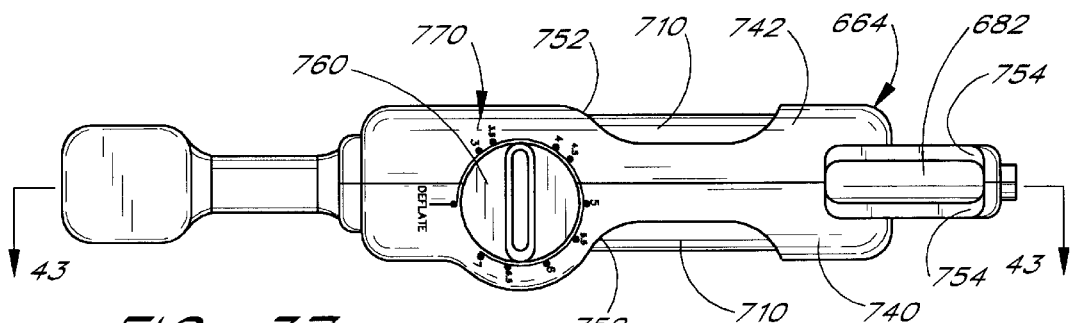
FIG. 37 is a top view of the device of FIG. 34.
Figure 38:
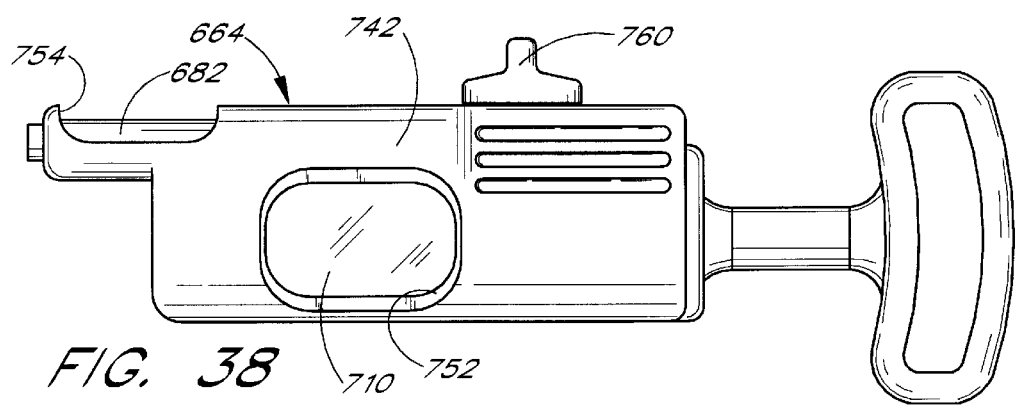
FIG. 38 is a left side view of the device of FIG. 34.
Figure 39:
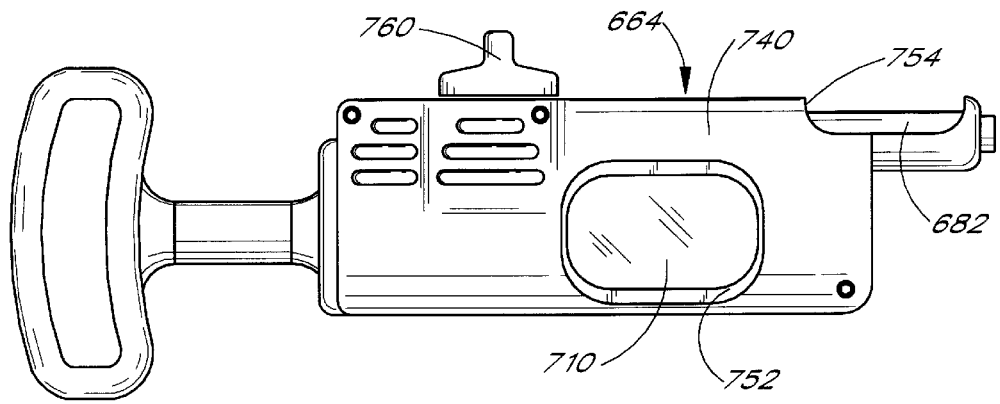
FIG. 39 is a right side view of the device of FIG. 34.
Figure 40:
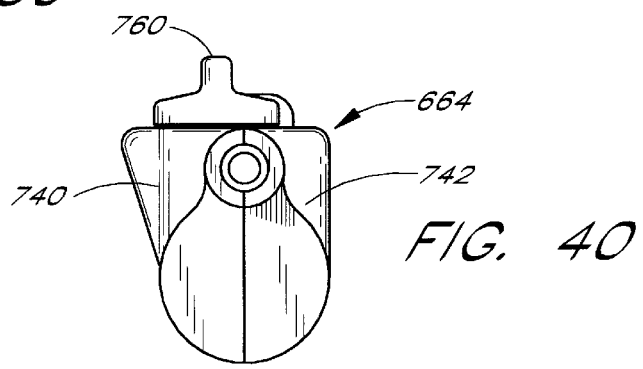
FIG. 40 is a front view of the device of FIG. 34.

FIG. 36 illustrates the present syringe assembly 650 without its housing 664. As shown, the inflation and reservoir syringes 660, 662 are preferably oriented side-by-side and in communication with each other through a channel 680.

With continued reference to FIG. 36, the inflation syringe 660 preferably has a capacity ranging between about 0.02 cc and 2 cc. The syringe 660 includes a hollow barrel 682 having an open proximal end 684 and a distal end 686 with an attachment portion 688 which can be connected to various medical components, such as a catheter, in any known manner. A port 690 is formed through the side of the barrel 682 between the proximal 684 and distal 686 ends.

The syringe 660 also includes a plunger 692 longitudinally slidable within the barrel 682 and sized and dimensioned to be at least partially positioned within the barrel 682. The plunger 692 includes an elongate shaft 694 with a distal end 696 and a proximal end 698. A piston 699 is disposed on the distal end 696 and is adapted to form a seal between the piston 699 and the inner surface of the barrel 682. The proximal end 698 of the plunger shaft 694 is preferably attached to a gear rack 700 having a plurality of gear teeth or ridges 702 formed thereon. Preferably, the gear pitch is about 48 and the gear rack 700 is about ⅛" thick. The gear rack 700 is preferably formed of modified molded nylon and alternatively could be formed of stainless steel.

The reservoir syringe 662 provides desirable power and volume for quickly priming the balloon and catheter. It is preferably of any conventional large volume syringe type with a capacity of between about 10–50 cc and more preferably about 40 cc. As shown in FIG. 36, the reservoir syringe 662 preferably has a generally cylindrical hollow barrel 710 having an open proximal end 712 and a tapered distal end 714. The tapered distal end 714 of the barrel 710 opens into the channel 680, which leads to the inflation syringe port 690.

The reservoir syringe 662 also includes a plunger 716 which is sized and dimensioned to be at least partially positioned within the hollow barrel 710. The plunger 716 includes an elongated shaft 718 which is generally circular in cross-section and is preferably constructed from material such as plastic or composites. A distal end 720 of the plunger shaft 718 includes a piston 722 which is adapted to form a seal between the piston 722 and the inner surface of the barrel 710. A handle 730 is formed at a proximal end 732 of the plunger 716. Preferably, the handle 730 is large, as illustrated in FIGS. 34–43, and is easily held in a clinician's hand.

Figure 41:
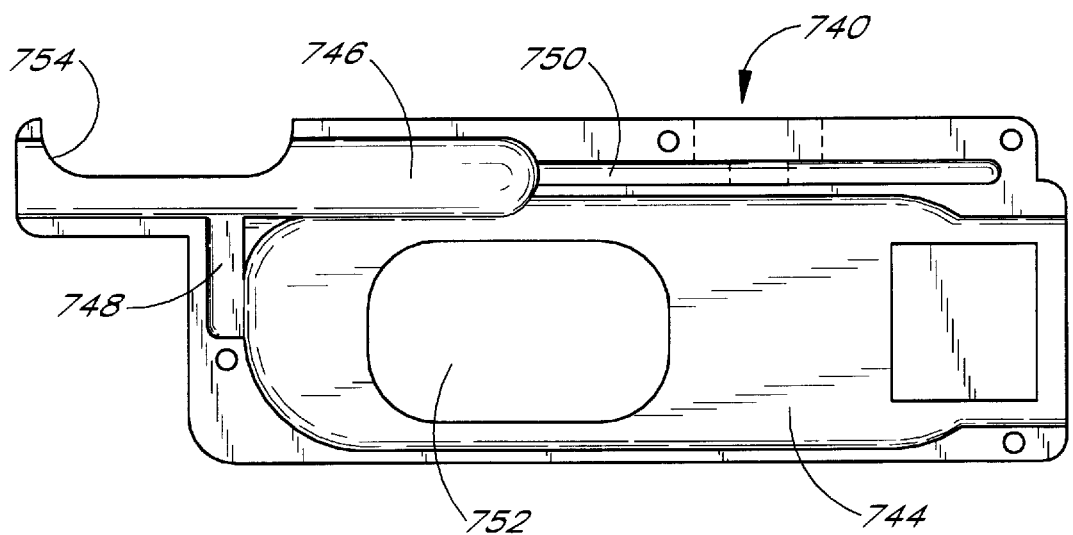
FIG. 41 is an inside view of the right housing of the device of FIG. 34.
Figure 42:
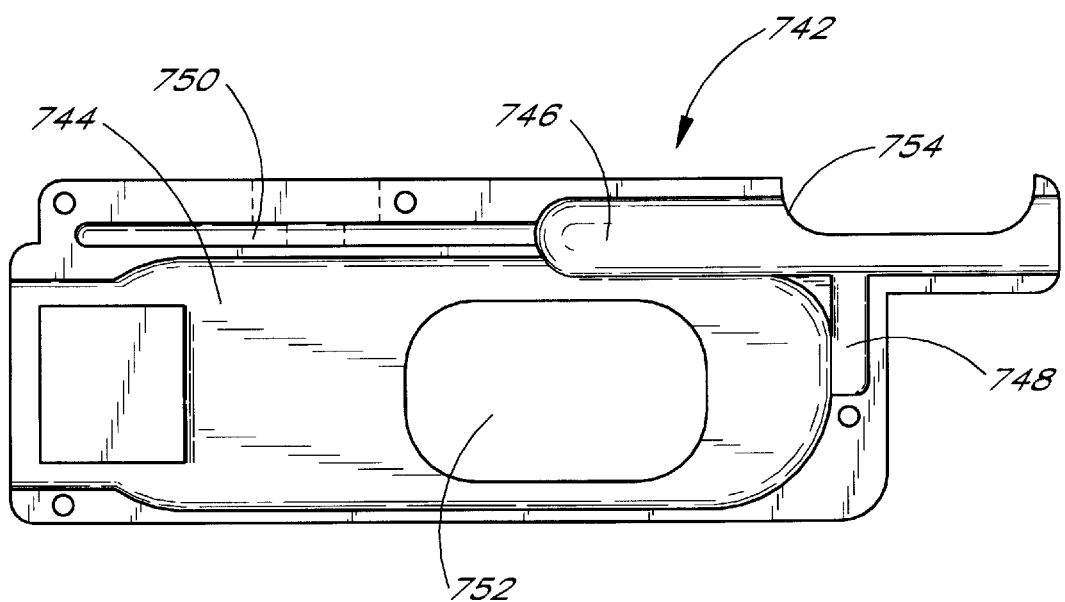
FIG. 42 is an inside view of the left housing of the device of FIG. 34.
Figure 43:
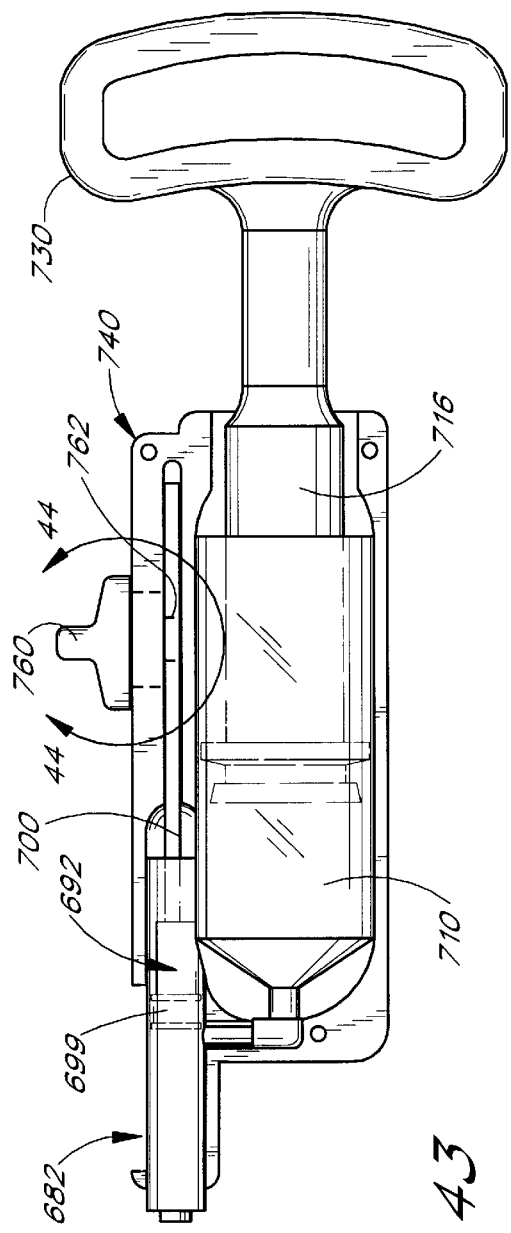
FIG. 43 is a cross-sectional view of the device of FIG. 37, taken along lines 43—43.

With next reference to FIGS. 37–42, the housing 664 preferably comprises a right half 740 and a left half 742 attached by screws, bolts, a sonic weld, or other means. The housing 664 is adapted to fit around the syringe assembly 650. With particular reference to FIGS. 41 and 42, each housing half 740, 742 has a large cavity 744 and a small cavity 746 to accommodate the large and small syringe barrels 710, 682, respectively. Each housing half 740, 742 further includes a channel cavity 748 and gear rack cavity 750 to accommodate the channel 680 and gear rack 700, respectively. FIG. 43 depicts the syringe assembly 650 disposed in a housing half 740.

With reference again to FIGS. 37–42, a large window 752 is formed through each housing half to allow the clinician to view the contents of the large syringe barrel 710. Similarly, a cutout 754 is formed in each housing half to allow the clinician to view the contents of the inflation syringe barrel 682.

Figure 44:
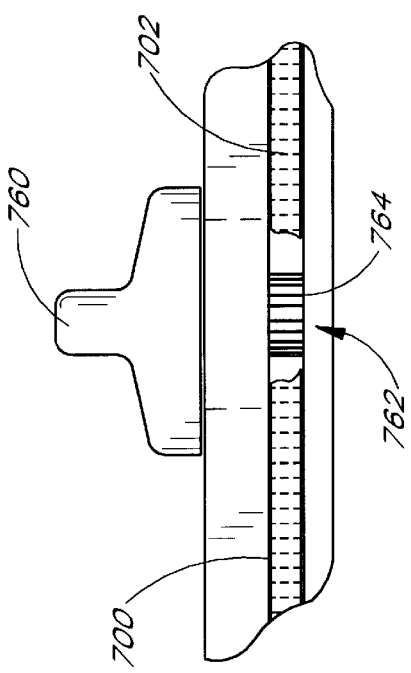
FIG. 44 is a cut-away view of the device of FIG. 43, taken along lines 44—44.

An inflation/deflation knob 760 is disposed on the outside of the housing 664. The inflation knob 760 is preferably formed of Delrin plastic but may also be preferably formed of metal or other plastics such as polycarbonate or ABS. With particular reference to FIGS. 43 and 44, the knob 760 is connected to a spur gear 762 having a pitch of about 48 and a pitch diameter of preferably about .292 inches. The spur gear 762 is adapted to engagingly mate the gear rack 700 attached to the inflation syringe 660. The teeth 764 of the spur gear 762, as shown in FIG. 44, communicate with the gear rack 700. Thus, when the knob 760 is rotated, the rotating spur gear 762 linearly moves the rack 700, thus advancing or retracting the plunger 692 within the inflation syringe barrel 682.

Referring again to FIG. 37, indicia 770 are preferably located on the housing 664 adjacent the knob 760 so that a clinician using the device can monitor the precise volume of liquid delivered by the inflation syringe 660. As depicted, the indicia 770 preferably comprise numbers corresponding to the size and shape of balloon used. When the knob 760 is rotated from the "DEFLATE" or "0" position to the number corresponding to the balloon in use, the syringe assembly 650 delivers the fluid volume associated with that balloon size. Alternatively, the indicia 770 could indicate the standard or metric volume of fluid delivered at each position.

To use the device, the inflation syringe plunger piston 699 is preferably first disposed immediately adjacent the proximal side of the port 690, as depicted in FIGS. 36 and 43. The knob 760 is positioned to correspond with the legend "DEFLATE" or "0" as indicated on the housing. The clinician connects the syringe assembly connector 666 to a source of balloon inflation fluid, preferably a diluted heparinized saline/contrast mixture, and retracts the large plunger 716 to fill the assembly 650 with 10–15 cc of fluid. Air is next purged from the syringe assembly 650 by holding the device vertically with the tip 686 pointing up and flushing air and air bubbles out by depressing the reservoir plunger 716. Excess fluid is flushed out, leaving about 5–10 cc of fluid.

The syringe assembly 650 is next connected to the occlusion catheter 70, preferably through an adapter 54 such as discussed above. The reservoir plunger 716 is then further retracted to prime the catheter. When priming, the reservoir plunger 716 is preferably held fully retracted for about 30 seconds until substantial all air within the catheter 70 has been aspirated. When the air is aspirated, the plunger 716 is slowly released to a neutral position.

When priming is complete and the surgical balloon is positioned as desired in the patient, the clinician rotates the knob 760 from the "DEFLATE" position to the desired setting corresponding to the balloon size and shape being used. Rotating the knob 760 moves the inflation syringe plunger 692 linearly towards the distal end 686 of the inflation syringe barrel 682, thus delivering inflation fluid to the balloon 72. To deflate the balloon, the knob 760 is rotated back to the "DEFLATE" position, thus linearly retracting the plunger 692 and drawing the inflation liquid back into the inflation syringe barrel 682.

Figure 45:
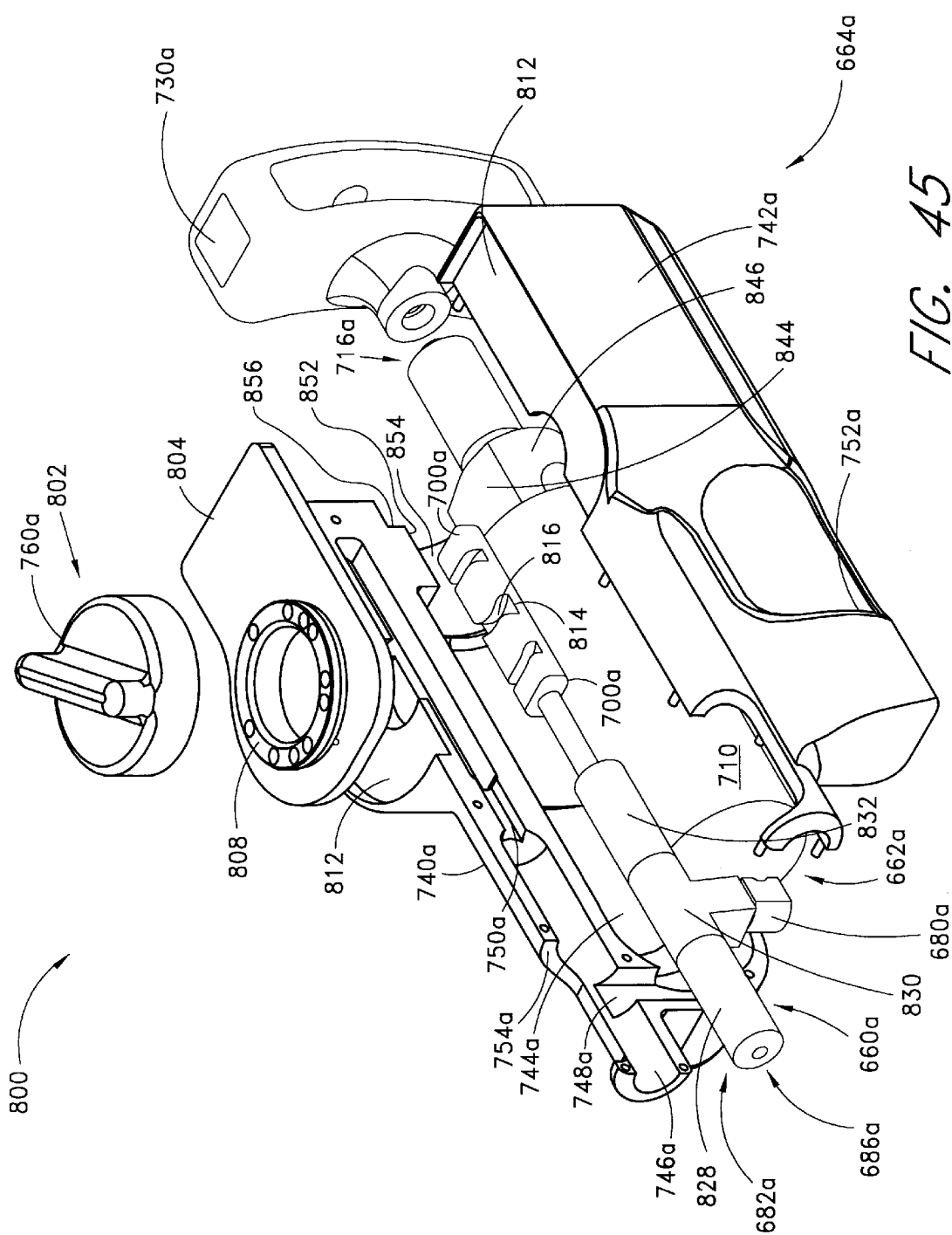
FIG. 45 is an exploded perspective view of another preferred embodiment of an integrated inflation/deflation device having features in accordance with the present invention.

With next reference to FIG. 45, an exploded perspective view of another embodiment of a syringe assembly 800 is disclosed. Syringe assembly 800 is similar in construction and operation to the syringe assembly 650 just discussed. Since syringe assembly 800 shares many similarities with the above syringe assembly 650, similar parts share part numbers; however, parts associated with syringe assembly 800 include the appellation "a".

Figure 46:
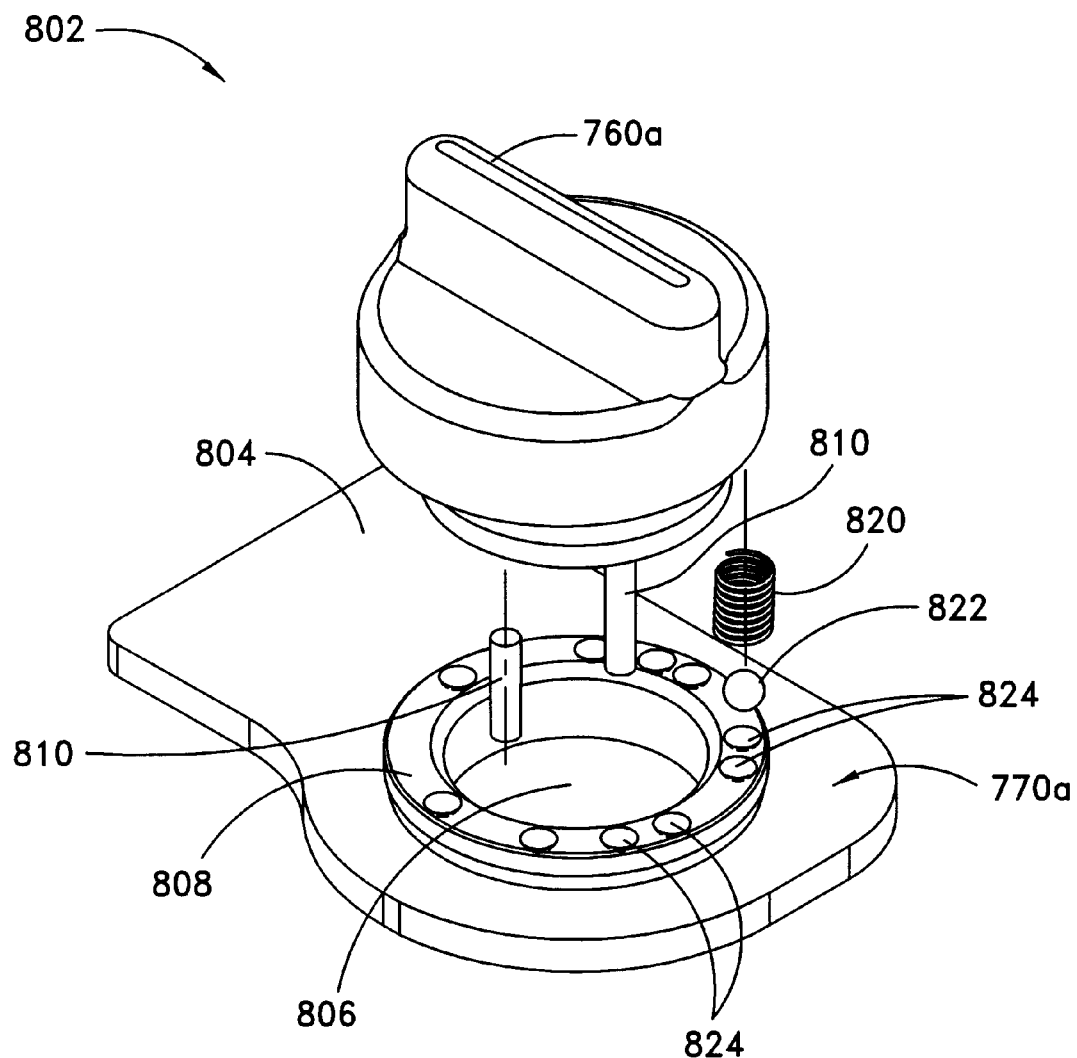
FIG. 46 is an exploded perspective view of a knob assembly for use with the device of FIG. 45.
Figure 47:
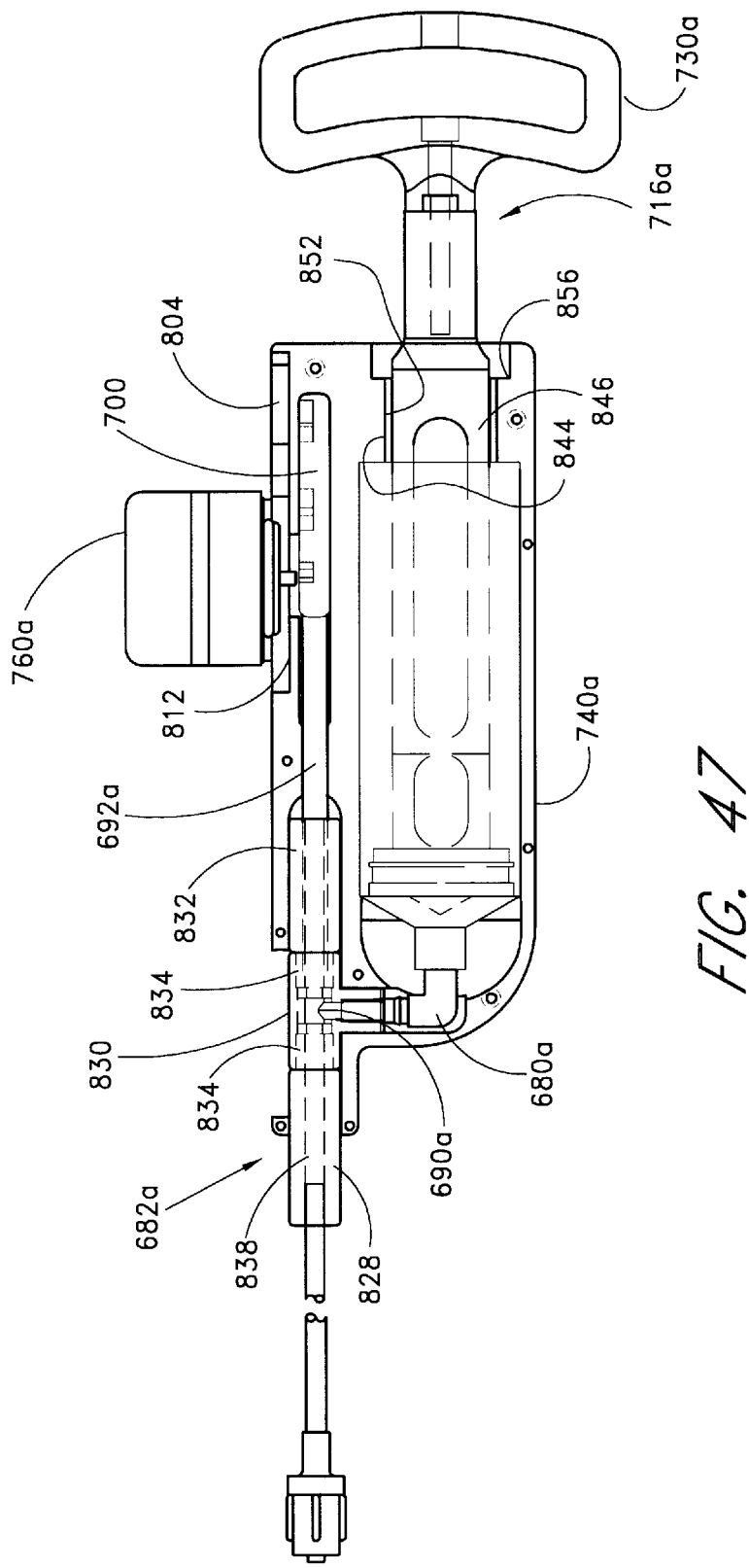
FIG. 47 is a top view of the device of FIG. 45.
Figure 48:
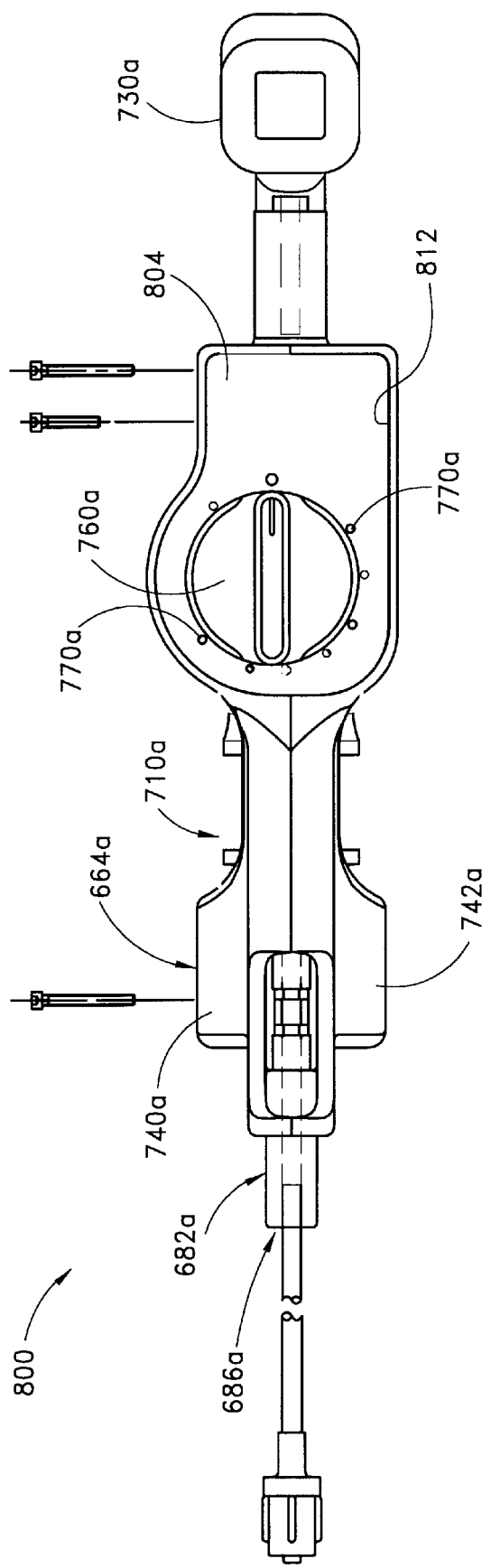
FIG. 48 is a side view of the device of FIG. 45, with a portion of the housing removed.

Referring next to FIG. 46, a knob assembly 802 is disclosed for use with the syringe assembly 800. The knob assembly 802 includes a knob plate 804 with an access hole 806 formed therethrough and a detent ring 808 encircling the hole 806. Indicia 770a are printed on the knob plate 804 adjacent the detent ring 808. At least two rods 810 depend from the knob 760a and are adapted to extend through the hole 806. Referring back to FIG. 45, the right and left halves 740a, 742a of the syringe assembly housing 664a each have a shallow cavity 812 formed in an upper portion. The cavity 812 is adapted to receive the knob plate 804 complementarily therewithin, as shown in FIGS. 47 and 48. Referring back to FIGS. 45 and 46, the rods 810 extend through the knob plate hole 806 to interact with a gear rack 700a which is attached to an inflation plunger 692a. As shown more particularly in FIGS. 45 and 49, the gear rack 700a preferably comprises a series of channels 814 sized and adapted to accept the rods 810 therein. The channels 814 and rods 810 are further adapted so that when the knob 760a is rotated, correspondingly moving the rods 810, the rods 810 move within the channels 814 and engage the channel walls 816 to advance or retract the attached inflation syringe plunger 692a.

Referring back to FIG. 46, the knob 760a has a detent hole (not shown) into which a spring 820 is placed. A ball 822 is placed in the hole with the spring 820. When the knob 760a is installed into the knob plate 804, the ball 822 is urged into contact with the detent ring 808. Cavities 824 are formed in the detent ring 808, each cavity 824 adjacent to a corresponding indicia mark 770a which, in turn, corresponds to a particular balloon size. Thus, as the knob 760a is rotated to any delineated indicia location, the spring 820 forces the ball 822 into the accompanying cavity 824, effectuating a detent.

Figure 50:
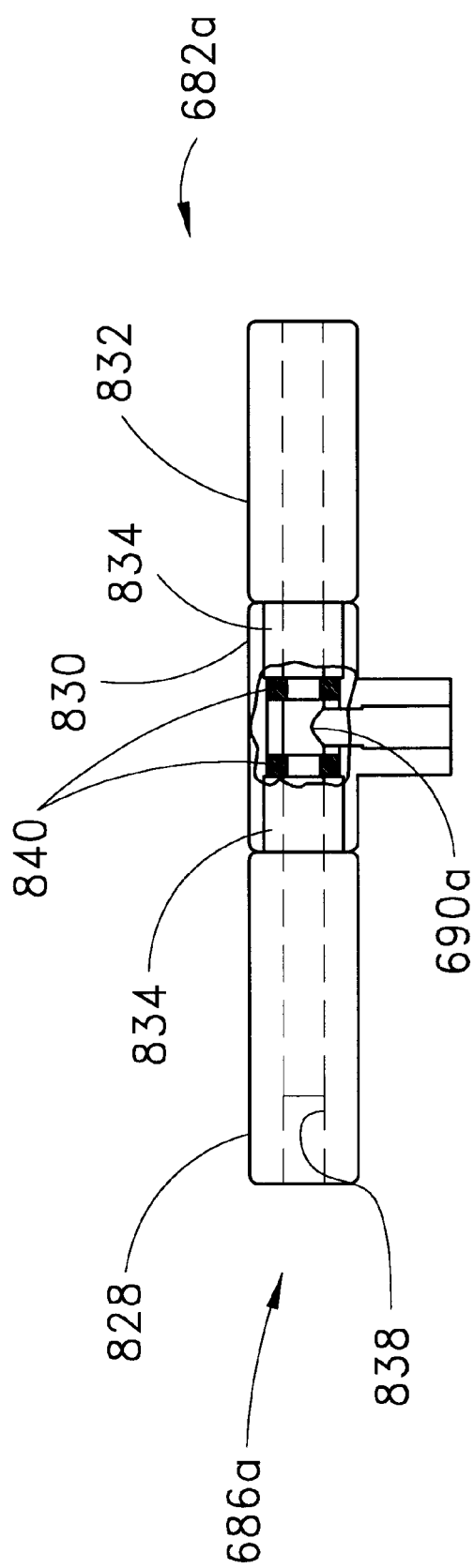
FIG. 50 is a partially cutaway detailed side view of an inflation barrel of the device of FIG. 45.

Referring back to FIG. 45, the syringe assembly 800 includes an inflation barrel 682a having a relatively low volume, preferably between about 0.02 cc–1.0 cc. The inflation barrel 682a preferably comprises a distal portion 828, medial portion 830, and proximal portion 832 mated together. Referring also to FIGS. 47 and 50, the medial portion 830 includes a port 690a which connects to the channel 680a between the reservoir syringe barrel 710a and the inflation barrel 682a. The distal portion 828 and proximal portion 832 each have a mating member 834 which fits complementarily into cavities formed in the medial portion 830, thus defining a continuous lumen 838 through the barrel 682a.

Figure 49:
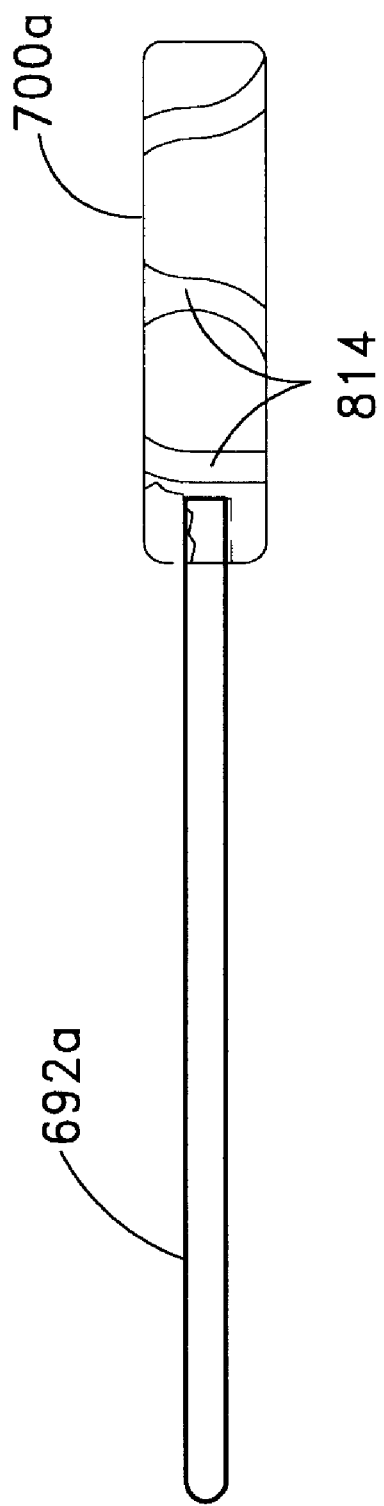
FIG. 49 is a top plan view of an inflation syringe plunger adapted for use with the device of FIG. 45.

Referring next to FIG. 49, the inflation plunger 692a extending from the gear rack 700a preferably comprises a substantially cylindrical precision-milled stainless steel rod.

With reference also to FIG. 50, the barrel 682a has a capacity ranging from between about 0.02 cc to 1.0 cc and most preferably between about 0.25 cc to 0.50 cc. The plunger 692a is adapted to slide freely within the barrel 682a. The medial portion 830 of the inflation barrel 682a preferably includes a pair of O-ring seals 840, one disposed on either side of the port 690a. The O-rings 840 are preferably sized to effect a seal with the inflation plunger 692a. In operation, when the inflation plunger 692a is advanced within the barrel 682a through the O-ring seals 840, the plunger displaces fluid within the barrel lumen 838. The displaced fluid is forced out of the barrel 682a through the distal end 686a, and is thus delivered to an attached balloon catheter. Since delivery of fluid is determined by the volume displaced by the plunger 692a, very small volumes may be precisely delivered without requiring the syringe barrel 682a to have a very small inner diameter that would require expensive manufacturing.

Thus, certain advantages of the embodiment of the present invention shown in FIGS. 47 and 50 are evident. In one aspect of this embodiment, the piston 834, as it is moved distally (or to the left in FIGS. 47 and 50) serves to seal the port 690a, thereby shutting off any access to the volumetric capacity of the reservoir syringe barrel 710a. In effect, then, this configuration eliminates the need or use of a stopcock which would typically be utilized in a two-separate-syringe embodiment. Accordingly, in this embodiment of the present invention, there is provided an automatic valve for communication with either the inflation barrel 682a or the reservoir syringe barrel 710a.

In another aspect of this embodiment, the inflation barrel 682a is situated so as to be distally oriented with respect to the reservoir syringe barrel 710a. This arrangement facilitates the automatic valve or sealing mechanism described in the previous paragraph, while still providing a long range of travel for the plunger 692a of the reservoir syringe barrel 710a.

Moreover, as best illustrated in FIG. 50, this longer range of travel, coupled with a minimized diameter of the plunger 692a of the inflation barrel 682a, provides for a very accurate syringe, in the sense that it is able to deliver very accurate and small volumes of fluid such as 0.05 cc, etc. This is achieved, in part, by fixing the O-ring seal 840, shown in FIG. 50, and allowing only the plunger 692a to pass through the O-ring 840. This means that the pressure of the inflation barrel 682a is determined by the diameter of the plunger and not by the entire outer diameter of the barrel 682a. In other words, if the O-ring were to move with the plunger 692a, the pressure, and therefore the volume of fluid delivered, would vary with the entire inner diameter of the inflation barrel 682a. With a smaller diameter plunger and a fixed O-ring, the smaller cross-sectional surface area defined by the diameter of the plunger allows the plunger to travel a greater distance while still delivering a smaller, accurate volume of fluid. Accordingly, it is easier to manufacture and to hold tolerances relative to a plunger rather than the inner diameter of a barrel or syringe.

Figure 51:
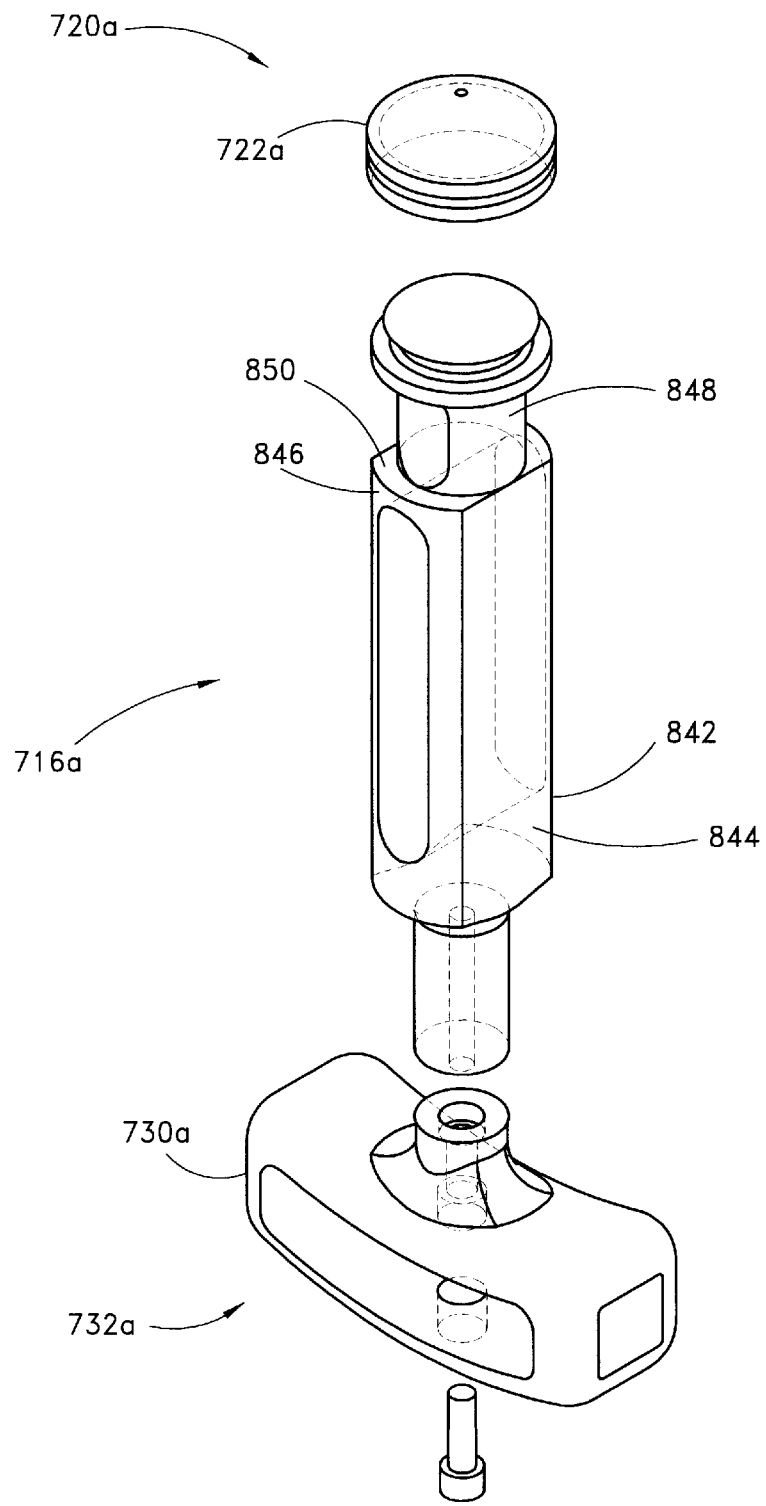
FIG. 51 is an exploded perspective view of a reservoir syringe plunger for use with the device of FIG. 45.

With reference next to FIG. 51, the reservoir syringe plunger 716a preferably has a main body 842 with two substantially flat opposing surfaces 844 and two arcuate opposing surfaces 846. A cylindrical distal portion 848 extends from a distal end of the main body 842. The distal cylinder 848 has a diameter substantially equal to the distance between the opposing flat surface 844; the diametrical distance between the arcuate surfaces 846 is greater than the distal cylinder 848 diameter. Thus, a distal notch 850 is defined between each arcuate surface 846 and the distal cylinder 848 surface.

Referring next to FIGS. 45 and 46, the housing 664a is adapted to complementarily receive the plunger main body 842. Specifically, the housing 664a has flat sides 852 which are complementary to the flat surfaces 844 of the main body, and arcuate sides 854 which complement the arcuate surfaces 846 of the plunger. This construction allows the plunger 746a to slide within the housing 664a, but not to rotate. A lock notch 856 is formed at the proximal end of the housing 664a. When the plunger 716a is retracted from the reservoir barrel 710a so that the plunger distal notch 850 is proximal the housing lock notch 856, the plunger main body 842 is free of the housing and the plunger may be rotated. When the plunger 716a is rotated about one-quarter turn, the plunger notch 850 will engage the housing lock notch 856, preventing the plunger 716a from advancing within the reservoir barrel 710a. Such a plunger lock is most useful during priming of the system and when deflating the balloon.

The syringe assembly 800 is preferably operated in conjunction with an inflation adapter 54 and balloon catheter 70 in a manner similar to the syringe assembly 650 discussed above. Once the balloon is inflated, the adapter is preferably actuated to close the catheter valve 66, thus maintaining balloon inflation. To deflate the balloon, the knob 760a is preferably rotated back to the "0" position, retracting the plunger 716a within the inflation barrel 682a, prior to opening the catheter valve 66. Once the catheter valve 66 is open, the reservoir plunger 716a is retracted to deflate the balloon. When fully retracted, the reservoir plunger 716a is rotated a quarter turn to engage the plunger distal notch 850 and housing lock notch 856 in order to lock the reservoir plunger 716a into place and correspondingly ensure the balloon and catheter remain deflated.

V. Alternative Uses for the Dual Syringe System

In addition to providing a highly responsive inflation system for an occlusion balloon, the dual syringe system also has a variety of other uses. For instance, the system could be used to deliver precise amounts of therapeutic drugs or medicine to the patient. The system may also be used for irrigation or aspiration. Additionally, the system can be used to infuse whole blood as is described below.

Typically, whole blood is infused into patients with roller type pumps. One problem associated with this type of pump is that roller mechanisms apply a shear stress that often damages the blood cells with the crushing force of the rollers. The dual syringe system could overcome the problem of damaging the blood by providing a hydrostatic pressure that would provide pressure for the transfusion without causing the damaging forces on the cells. The blood cells, because of their circular shape, can withstand great hydrostatic pressure and therefore would not be damaged. Preferably, the large volume syringe will be used to infuse blood.

A low volume syringe or syringe assembly having features in accordance with the present invention is not limited to use only with the inflation adapter as presented herein. Other arrangements or assemblies may include syringe embodiments of the present invention. Similarly, the method of the present invention may omit the use of an inflation adapter without loss of benefit from the present invention.

The embodiments of the apparatus and method as described above are provided merely to illustrate the present invention. Changes and modifications may be made from the embodiments presented herein by those skilled in the art without departure from the spirit and scope of the invention, as defined by the appended claims.

What is claimed is:

1. A syringe assembly for use with a low volume surgical balloon attached at a distal portion of an elongated tube, the tube having a proximal portion, a sealed distal end and an inflation lumen extending therebetween for communicating fluid to the balloon, the assembly comprising:

a low volume syringe with an elongated, hollow body having proximal and distal ends, a connector on the distal end, a port formed through the body between the proximal and distal ends, and a plunger longitudinally slidable within the body and a gear rack extending proximally from a plunger proximal end;

a large volume syringe having a relatively large fluid capacity and comprising an elongated, hollow body having proximal and distal ends, a plunger longitudinally slidable within the body and having a shaft with a piston disposed on a large shaft distal end and a handle disposed on a large shaft proximal end, and the large syringe body distal end has an opening in communication with a channel leading to the low volume syringe port; and a housing adapted to substantially enclose both the low volume syringe and the large syringe, the housing including a knob having at least one protrusion adapted to engage said gear rack.

2. The syringe assembly of claim 1, further including at least one sealing member within the low volume syringe barrel, and the sealing member is adapted to create a fluid seal about the low volume plunger.

3. The syringe assembly of claim 2, wherein one of the sealing members is positioned within the low volume syringe barrel on a proximal side of the port and another is positioned on a distal side of the port.

4. The syringe assembly of claim 2, wherein the at least one sealing member comprises an elastic O-ring.

5. The syringe assembly of claim 1, further including a detent mechanism for releasably securing the knob in at least one position.

6. The syringe assembly of claim 1, further including indicia disposed about the knob to indicate the volume of fluid communicated to the balloon corresponding to a position of the knob.

7. The syringe assembly of claim 6, wherein rotation of the knob from a first position to an indicated balloon volume position delivers a precise, accurate volume of fluid to the balloon.

8. The syringe assembly of claim 7, wherein rotation of the knob from the balloon volume position back to the first position evacuates the fluid from the balloon into the syringe assembly.

9. The syringe assembly of claim 1, wherein the protrusion comprises a gear adapted to engage the gear rack.

10. The syringe assembly of claim 1, wherein the low volume syringe and the large syringe are disposed in the housing in a substantially parallel relation.

11. A method of using the syringe assembly of claim 1, comprising the steps of:

positioning the knob at a deflation position at which the low volume syringe piston is disposed adjacent a proximal edge of the port;

providing a source of inflation fluid for the balloon;

attaching the distal connector to the source of inflation fluid;

pulling on a proximal end of the large volume syringe handle to fill the syringe with a predetermined volume of inflation fluid;

detaching the distal connector from the source of inflation fluid;

attaching the distal connector to the elongated tube so that the syringe is in communication with the tube lumen; and rotating the knob to a predetermined position;

whereby the syringe assembly delivers a predetermined amount of fluid as defined by the predetermined position.

12. The method of claim 11, further including the step of pulling on the large volume syringe plunger after the distal connector is attached to the elongated tube to effect evacuation of air or fluid within the tube lumen, the balloon and the low volume syringe into the large syringe.

13. A syringe assembly adapted for use in medical procedures requiring relatively accurate volumetric delivery of fluids, comprising:

an inflation syringe with an inflation lumen having proximal and distal ends, a connector at the distal end, and a port formed through a side of the inflation lumen between the proximal and distal ends;

a first plunger having proximal and distal ends and longitudinally slidable within the inflation lumen to effect fluid intake and outflow;

a reservoir syringe having a reservoir lumen with proximal and distal ends, the distal end in communication with said port; and a second plunger having proximal and distal ends and longitudinally slidable within the reservoir lumen.

14. The syringe assembly of claim 13, wherein the inflation lumen and reservoir lumen are oriented side-by-side and are enclosed within a single housing.

15. The syringe assembly of claim 14, including a knob connected to a spur gear and a gear rack in communication with the first plunger, and the knob is positioned on the housing such that the spur gear engages the gear rack.

16. The syringe assembly of claim 14, including a knob in communication with at least one protrusion and a gear rack in communication with the first plunger, the knob positioned on the housing such that the at least one protrusion engages the gear rack, and the knob, protrusion, and gear rack adapted so that rotation of the knob moves the protrusion, and the moving protrusion linearly moves the gear rack.

17. The syringe assembly of claim 16, wherein the knob includes a detent mechanism.

18. The syringe assembly of claim 17, wherein the detent mechanism comprises a spring and ball disposed at least partially within a cavity.

19. The syringe assembly of claim 13, including a sealing member within said inflation lumen and proximal said port, the sealing member adapted to effect a fluid seal about the first plunger.

20. The syringe assembly of claim 19, including a second sealing member within said inflation lumen and distal said port.

21. The syringe assembly of claim 20, wherein the first and second sealing members comprise resilient O-rings.

22. The syringe assembly of claim 21, wherein said plunger is substantially cylindrical.

23. A method of easily and precisely inflating a balloon catheter comprising an elongated tube having a proximal portion and a sealed distal end with a surgical balloon attached thereto, the tube having a longitudinally extending lumen communicating with the balloon for inflation thereof, the method comprising:

inserting and positioning the tube and balloon at a desired position within a blood vessel of a patient;

providing a syringe assembly comprising an inflation syringe having an inflation lumen and a reservoir syringe having a reservoir lumen;

providing a port through a side of the inflation lumen;

providing a channel connecting a distal end of the reservoir lumen to the inflation lumen port;

providing an inflation plunger within the inflation lumen and a reservoir plunger within the reservoir lumen;

positioning the inflation plunger so that a distal end of the inflation plunger is adjacent a proximal side of the port;

connecting the proximal portion of the tube to a distal end of the inflation lumen;

pulling on the reservoir plunger to effect evacuation of air or fluid within the tube and the balloon into the reservoir lumen; and pushing the inflation plunger to deliver the predetermined amount of fluid to the tube and balloon;

whereby the fluid inflates the balloon to an appropriate size without rupture of the balloon or damage to the blood vessel of the patient.

24. The method of claim 23, further comprising the steps of:

providing a housing enclosing the inflation syringe;

providing a knob extending through the housing and in communication with a protrusion inside the housing;

providing a gear rack attached to the inflation plunger and adapted to engage the protrusion; and rotating the knob to a predetermined point;

whereby rotation of the knob moves the protrusion, thus advancing the gear rack and pushing the inflation plunger to deliver a precise volume of fluid.

25. The method of claim 23, further comprising the step of providing inflation fluid to the inflation lumen.

* * * * *